(12) United States Patent
Bis et al.

(10) Patent No.: US 9,687,497 B1
(45) Date of Patent: Jun. 27, 2017

(54) SALTS AND POLYMORPHS OF CYCLIC BORONIC ACID ESTER DERIVATIVES AND THERAPEUTIC USES THEREOF

(71) Applicant: Rempex Pharmaceuticals, Inc., San Diego, CA (US)

(72) Inventors: Joanna A. Bis, Cary, NC (US); Pingyun Chen, Chapel Hill, NC (US); Senthil Kumar Kusalakumari Sukumar, Raleigh, NC (US)

(73) Assignee: Rempex Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 15/309,425

(22) PCT Filed: Apr. 29, 2015

(86) PCT No.: PCT/US2015/028265
§ 371 (c)(1),
(2) Date: Nov. 7, 2016

(87) PCT Pub. No.: WO2015/171398
PCT Pub. Date: Nov. 12, 2015

Related U.S. Application Data

(60) Provisional application No. 61/988,524, filed on May 5, 2014.

(51) Int. Cl.
*A61K 31/69* (2006.01)
*C07F 5/02* (2006.01)
*A61K 31/397* (2006.01)
*A61K 31/545* (2006.01)

(52) U.S. Cl.
CPC ........... *A61K 31/69* (2013.01); *A61K 31/397* (2013.01); *A61K 31/545* (2013.01); *C07F 5/025* (2013.01); *A61K 2121/00* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 4,194,047 A | 3/1980 | Christensen et al. | |
| 4,260,543 A | 4/1981 | Miller | |
| 4,409,214 A | 10/1983 | Takaya et al. | |
| 4,822,786 A | 4/1989 | Zama et al. | |
| 5,442,100 A | 8/1995 | Bjorkquiest et al. | |
| 5,888,998 A | 3/1999 | Maiti et al. | |
| 6,184,363 B1 | 2/2001 | Shoichet et al. | |
| 6,586,615 B1 | 7/2003 | Kettner et al. | |
| 7,271,186 B1 | 9/2007 | Shoichet et al. | |
| 7,439,253 B2 | 10/2008 | Lampilas et al. | |
| 7,582,621 B2 | 9/2009 | Baker et al. | |
| 7,612,087 B2 | 11/2009 | Aszodi et al. | |
| 9,012,491 B2 | 4/2015 | Reddy et al. | |
| 9,101,638 B2 | 8/2015 | Reddy et al. | |
| 9,132,140 B2 | 9/2015 | Reddy et al. | |
| 9,156,858 B2 | 10/2015 | Reddy et al. | |
| 9,296,763 B2 | 3/2016 | Hirst et al. | |
| 9,511,142 B2 | 12/2016 | Burns et al. | |
| 2004/0019203 A1 | 1/2004 | Micetich et al. | |
| 2004/0157826 A1 | 8/2004 | Lampilas et al. | |
| 2005/0020572 A1 | 1/2005 | Aszodi et al. | |
| 2006/0019116 A1 | 1/2006 | Conley et al. | |
| 2006/0178357 A1 | 8/2006 | Buynak et al. | |
| 2006/0210883 A1 | 9/2006 | Chen et al. | |
| 2010/0056478 A1 | 3/2010 | Desarbre et al. | |
| 2010/0120715 A1 | 5/2010 | Burns et al. | |
| 2010/0256092 A1 | 10/2010 | Xia et al. | |
| 2011/0288063 A1 | 11/2011 | Maiti et al. | |
| 2012/0040932 A1 | 2/2012 | Hirst et al. | |
| 2013/0316978 A1 | 11/2013 | Reddy et al. | |
| 2013/0331355 A1 | 12/2013 | Griffith et al. | |
| 2013/0345172 A1 | 12/2013 | Hirst et al. | |
| 2014/0194381 A1 | 7/2014 | Reddy et al. | |
| 2014/0194382 A1 | 7/2014 | Reddy et al. | |
| 2014/0194384 A1 | 7/2014 | Reddy et al. | |
| 2014/0194385 A1 | 7/2014 | Reddy et al. | |
| 2014/0194386 A1 | 7/2014 | Burns et al. | |
| 2014/0206648 A1 | 7/2014 | Reddy et al. | |
| 2015/0119363 A1 | 4/2015 | Dudley et al. | |
| 2016/0220591 A1 | 8/2016 | Hirst et al. | |
| 2016/0339045 A1 | 11/2016 | Griffith et al. | |

FOREIGN PATENT DOCUMENTS

| | | | |
|---|---|---|---|
| EP | 1550657 A1 | 7/2005 | |
| EP | 2508506 A1 | 10/2012 | |
| FR | 2573070 A1 | 5/1986 | |

(Continued)

OTHER PUBLICATIONS

Livermore et al., "Activity of biapenem (RPX2003) combined with the boronate beta-lactamase inhibitor RPX7009 against carbapenem-resistant Enterobacteriaceae", J Antimicrob Chemother. (Aug. 2013) 68(8):1825-1831.

International Search Report and Written Opinion dated Jul. 1, 2015 for Application No. PCT/US2015/028265, filed Apr. 29, 2015.

International Preliminary Report on Patentability (Chapter I) dated Nov. 17, 2016 for International Application No. PCT/US2015/028265, filed Apr. 29, 2015.

Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.

Adediran et al., "A 'cephalosporin-like' cyclic depsipeptide: Synthesis and reaction with beta-lactam-recognizing enzymes", Bioorg Med Chem Lett. (1999) 9(3):341-346.

(Continued)

*Primary Examiner* — Michael Barker
(74) *Attorney, Agent, or Firm* — Knobbe Marten Olson & Bear LLP

(57) ABSTRACT

Disclosed herein is the crystalline form of the potassium salt of 2-((3R,6S)-2-hydroxy-3-(2-(thiophen-2-yl)acetamido)-1,2-oxaborinan-6-yl)acetic acid. The crystalline form maybe formulated for treating subjects with bacterial infection. Accordingly, some embodiments relate to compositions and methods of administering the potassium salt of 2-((3R,6S)-2-hydroxy-3-(2-(thiophen-2-yl)acetamido)-1,2-oxaborinan-6-yl)acetic acid.

24 Claims, 8 Drawing Sheets

(56) References Cited

FOREIGN PATENT DOCUMENTS

| | | |
|---|---|---|
| JP | 2003-229277 | 8/2003 |
| JP | 2004-291253 | 10/2004 |
| WO | WO 87/05297 | 9/1987 |
| WO | WO 89/10961 | 11/1989 |
| WO | WO 98/56392 A1 | 12/1998 |
| WO | WO 00/35904 A1 | 6/2000 |
| WO | WO 00/35905 A1 | 6/2000 |
| WO | WO 01/23374 A1 | 4/2001 |
| WO | WO 01/30149 | 5/2001 |
| WO | WO 02/22137 A1 | 3/2002 |
| WO | WO 02/083884 | 10/2002 |
| WO | WO 03/070714 | 8/2003 |
| WO | WO 2004/039859 | 5/2004 |
| WO | WO 2004/058679 A2 | 7/2004 |
| WO | WO 2004/064755 A2 | 8/2004 |
| WO | WO 2005/033090 | 4/2005 |
| WO | WO 2005/035532 A1 | 4/2005 |
| WO | WO 2005/087700 | 9/2005 |
| WO | WO 2006/052733 A1 | 5/2006 |
| WO | WO 2006/091771 | 8/2006 |
| WO | WO 2007/058602 A2 | 5/2007 |
| WO | WO 2007/065288 A2 | 6/2007 |
| WO | WO 2007/095638 | 8/2007 |
| WO | WO 2008/039420 A2 | 4/2008 |
| WO | WO 2008/116813 A1 | 10/2008 |
| WO | WO 2009/046098 A1 | 4/2009 |
| WO | WO 2009/064413 A1 | 5/2009 |
| WO | WO 2009/064414 A1 | 5/2009 |
| WO | WO 2009/091856 A1 | 7/2009 |
| WO | WO 2009/117540 A1 | 9/2009 |
| WO | WO 2009/139834 A1 | 11/2009 |
| WO | WO 2009/140309 A2 | 11/2009 |
| WO | WO 2010/056827 A1 | 5/2010 |
| WO | WO 2010/075286 A1 | 7/2010 |
| WO | WO 2010/097675 A1 | 9/2010 |
| WO | WO 2010/130708 A1 | 11/2010 |
| WO | WO 2010/144338 A1 | 12/2010 |
| WO | WO 2011/017125 A1 | 2/2011 |
| WO | WO 2011/103686 A1 | 9/2011 |
| WO | WO 2011/123502 A1 | 10/2011 |
| WO | WO 2012/021455 A1 | 2/2012 |
| WO | WO 2012/058065 A1 | 5/2012 |
| WO | WO 2012/067664 A1 | 5/2012 |
| WO | WO 2012/106995 A1 | 8/2012 |
| WO | WO 2012/136383 A1 | 10/2012 |
| WO | WO 2013/033461 A1 | 3/2013 |
| WO | WO 2013/053372 A1 | 4/2013 |
| WO | WO 2013/056163 A1 | 4/2013 |
| WO | WO 2013/092979 A1 | 6/2013 |
| WO | WO 2013/104774 A1 | 7/2013 |
| WO | WO 2013/107897 A1 | 7/2013 |
| WO | WO 2013/122888 A2 | 8/2013 |
| WO | WO 2013/184845 A1 | 12/2013 |
| WO | WO 2014/089365 A1 | 6/2014 |
| WO | WO 2014/107535 A1 | 7/2014 |
| WO | WO 2014/107536 A1 | 7/2014 |
| WO | WO 2014/110442 A1 | 7/2014 |
| WO | WO 2014/151958 A1 | 9/2014 |
| WO | WO 2015/171398 A1 | 11/2015 |
| WO | WO 2015/179308 A1 | 11/2015 |
| WO | WO 2016/003929 A1 | 1/2016 |
| WO | WO 2016/065282 A1 | 4/2016 |

OTHER PUBLICATIONS

Aizpurua et al., "Synthesis of benzyl halides from aldehydes promoted by halosilanes and 1,1,3,3-tetramethyldisiloxane (TMDS)", Tetrahedron Lett. (1984) 25(10):1103-1104.
Akiyama et al., "N-Hydroxy Amides. Part 6. Synthesis and Spectroscopic Properties of 1-Hydroxypiperazine-2,5-diones", J Chem Soc., Perkin Trans I, (1989) 2:235-239.
Allen et al., "Ansel's Pharmaceutical Dosage Forms and Drug Delivery Systems", 8th Edition (2004) TOC only.
American Chemical Society. STN Chemical Database Registry RN: 1226917; Jun. 2010; 2 pages.
Arya et al., "Advances in asymmetric enolate methodology", Tetrahedron (2000) 56:917-947.
Babic et al., "What's new in antibiotic resistance? Focus on beta-lactamases", Drug Res Updates (2006) 9:142-156.
Bassetti et al., "New antibiotics for bad bugs: where are we?", Ann Clin Microbiol Antimicrob. (2013) 12:22-36.
Becker, Daniel E., "Antimicrobial Drugs", Anesth Prog (2013) 60:111-123.
Beenen et al., "Asymmetric copper-catalyzed synthesis of alpha-amino boronate esters from N-tert-butanesulfinyl aldimines", J Am Chem Soc. (2008) 130(22):6910-6911.
Biedrzycki et al., "Derivatives of tetrahedral boronic acids", J. Organomet. Chem. (1992) 431:255-270.
Bou et al., "Cloning, nucleotide sequencing, and analysis of the gene encoding an AmpC beta-lactamase in Acinetobacter baumannii", Antimicrob Agents Chemother (2000) 44(2):428-432.
Bou et al., "OXA-24, a novel class D beta-lactamase with carbapenemase activity in an Acinetobacter baumannii clinical strain", Antimicrob Agents Chemother (2000) 44(6):1556-1561 and Erratum: Antimicrob Agents Chemother. (2006) 50(6) 2280.
Brabez et al., "Design,synthesis, and biological studies of efficient multivalent melanotropin ligands: tools toward melanoma diagnosis and treatment", J Med Chem. (2011) 54(20):7375-7384.
Brosz et al., "Resolution of alpha-aminoboronic esters by diastereoselective crystallization with pinanediols. Confirmation by x-ray analysis", Tetrahedron: Asymmetry (1997) 8(9):1435-1440.
Bush et al., "Minireview: Updated Functional Classification of beta-Lactamases," Antimicrob Agents Chemo. (2010) 54(3):969-976.
CAS Registry Nos. 69190-59/60 (2-(bis(phenylthio)methyl)-4,4,5,5-tetramethyl-1,3,2-dioxaborolane) and 69190-60-9 (2-(bis(phenylthio)methyl)-1,3,2-dioxaborinane) Scheme 18 (2015); 2 pages.
CAS Registry No. 105892-95-3 Boronic acid [1-(phenylsulfonyl)heptyl]-, dimethyl ester (2015); 2 pages.
Cheng et al., "Synthesis of Aryl Thioethers through the N-Chlorosuccinimide-Promoted Cross-Coupling Reaction of Thiols with Grignard Reagents", J Org Chem. (2012) 77(22):10369-10374.
Chemicalland21.com. "Meglumine", Jun. 7, 2011. Downloaded from </www.chemicalland21.com/lifescience/phar/N-METHYL-D-GLUCAMINE.htm>; 2 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2006) M7-A7 26(2), 64 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2009) M07-A8 29(2), 88 pages.
Clinical Trial NCT02168946, "A Phase 3, Multi-Center, Randomized, Open-Label Study of Carbavance (Meropenem/RPX7009) Versus Best Available Therapy in Subjects with Selected Serious Infecations Due to Carbapenem-Resistant Enterobacteriaceae", Oct. 6, 2014; retrieved online from URL:https://clinicaltrials.gov/archive/NCT02168946/20140_10_06.
Conte et al., "Intrapulmonary pharmacokinetics and pharmacodynamics of meropenem", Int J Antimicrob Agents (Dec. 2005) 26(6):449-456.
Coppa et al., "A Facile, Convenient and Selective Homolytic Carbamolylation of Heteroaromatic Bases", Heterocycles (1993) 36(12):2687-2696.
Coutts et al., "Two Efficient Methods for The Cleavage of Pinanediol Boronate Esters Yielding The Free Boronic Acids", Tetrahedron Lett. (1994) 35(29):5109-5112.
Danziger et al., "Automated Site-directed Drug Design: A General Algorithm for Knowledge Acquisition about Hydrogen-bonding Regions at Protein Surfaces", Proc. Royal Soc London, Series B, Biol. Sciences (1989) 236(1283):101-113.
Darses et al., "Potassium Organotrifluoroborates: New Perspectives in organic Synthesis", Chem Rev. (2008) 108:288-325.

(56) References Cited

OTHER PUBLICATIONS

Davoli et al., "Enantioselective total synthesis of (−)-microcarpalide", Tetrahedron (2005) 61:4427-4436.
de Meijere A. [Ed], Science of Synthesis—vol. 24; "Three Carbon-Heteroatom Bonds: Ketene Acetals and Yne-X Compounds", TOC 46 pages.
Di Gioia et al., "Optically Pure N-Hydroxy-O-triisopropylsilyl-alpha-L-amino Acid Methyl Esters from AlCl3-Assisted Ring Opening of Chiral Oxaziridines by Nitrogen Containing Nucleophiles", J Org Chem. (2005) 70(25):10494-10501.
Drawz et al., "Three Decades of beta-Lactamase Inhibitors", Clin Microbiol Reviews (Jan. 2010) 23(1):160-201.
Eidam et al., "Design, synthesis, crystal structures and antimicrobial activity of sulfonamide boronic acids as beta-lactamase inhibitors", J Med Chem. (2010) 53(21):7852-7863.
Eissenstat et al., "Aminoalkylindoles: Structure-Activity Relationships of Novel Cannabinoid Mimetics", J Med Chem. (1995) 38(16):3094-3105.
El Nezhawy et al., "Synthesis and antioxidant activity of some thiazolidin-4-one derivatives", Springer; Chemical Monthly/Monatshefte für Chemie (2009) 140(5):531-539.
Endo et al., "Chemoselective Suzuki coupling of diborylmethane for facile synthesis of benzylboronates", Org Lett. (2011) 13(13):3368-3371.
Fan, et al. (2009): STN International HCAPLUS database, Columbus (OH), accession No. 2009: 425839; 6 pages.
Farquhar et al., "Intensely potent doxorubicin analogues: structure-activity relationship", J. Med. Chem. (1998) 41(6):965-972.
Ghosh et al., "Enantioselective total synthesis of (+)-largazole, a potent inhibitor of histone deacetylase", Org Lett. (2008) 10(17):3907-3909.
Giroux, A., "Synthesis of benzylic boronates via palladium-catalyzed cross-coupling reaction of bis(pinacolato)diboron with benzylic halides", Tetrahedron Lett. (2003) 44:233-235.
Gorovoy et al., "Boron-Containing Peptidomimetics—A Novel Class of Selective Anti-tubercular Drugs", Chem Biol Drug Des. (Jan. 2013) 81(3):408-413.
Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.
Graham et al., "D is for Drugs", Chemistry & Industry, Mar. 19, 2013, pp. 28-30, Downloaded from http://www.concertpharma.com/wp-content/uploads/2014/12/ChemistryIndustry-0313.pdf; 3 pages.
Greene, et al., "*Greene's Protective Groups in Organic Synthesis*", 4th Edition, (2007); pp. 774, 785 & 787.
Hama et al., "Palladium-Catalyzed alpha-Arylation of Zinc Enolates of Esters: Reaction Conditions and Substrate Scope", J Org Chem. (2013) 78(17):8250-8266.
Hecker et al., "Discovery of a Cyclic Boronic Acid beta-Lactamase Inhibitor (RPX7009) with Utility vs Class A Serine Carbapenemases", J Med Chem. (Mar. 2015) 58:3682-3692.
Imanishi et al., "Discovery of a Novel Series of Biphenyl Benzoic Acid Derivatives as Potent and Selective Human beta3-Adrenergic Receptor Agonists with Good Oral Bioavailability. Part I", J Med Chem. (2008) 51(6):1925-1944.
Inglis et al., "Observations on the Deprotection of Pinanediol and Pinacol Boronate Esters via Fluorinated Intermediates", J Org Chem. (2010) 75(2):468-471.
Ishii et al, "In vitro potentiation of carbapenems with ME1071, a Novel metallo-β-lactamase inhibitor, against metallo-β-lactamase producing pseudomonas aeruginosa clinical isolates." Antimicrob. Agents Chemother. doi:10.1128/AAC.01397-09 (2010) 54(9):3625-3629.
Ito et al., "An efficient constructive method for a tricyclic system: an important intermediate for the synthesis of tricycloclavulone", Tetrahedron Lett. (2003) 44:1259-1261.

Jadhav et al., "Direct synthesis of [alpha-[(tert-Butoxycarbonyl)amino]alkyl]-boronates from (alpha-Haloalkyl)boronates", Org Chem. (1996) 61(22):7951-7954.
Jagannathan et al., "Synthesis of Boronic Acid Analogues of alpha-Amino Acids by Introducing Side Chains as Electrophiles", J Org Chem. (2001) 66(19):6375-6380.
Jiang et al., "A Practical Synthesis of Cefcapene Pivoxil", Synthesis (2012) 44:207-214.
Johnson et al., "A drug targeting motif for glycosidase inhibitors: An iminosugar-boronate shows unexpectedly selective beta-galactosidase inhibition", Tetrahed Lttrs. (2002) 43(49):8905-8908.
Kabalka et al., "Synthesis of a series of bornonated unnatural cyclic amino acids as potential boron neutron capture therapy agents", Appl Organomet Chem. (2008) 22(9):516-522.
Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", Chem Letts. (1993) 22(5):845-848.
Kawamorita et al., "Synthesis of Primary and Secondary Alkylboronates through Site-Selective C(sp3)-H Activation with Silica-supported Monophosphine-Ir Catalysts", J Am Chem Soc. (2013) 135(8):2947-2950.
Kikuchi et al., "Comparison of the Pharmacodynamics of Biapenem in Bronchial Epithelial Lining Fluid in Healthy Volunteers Given Half-Hour and Three-Hour Intravenous Infusions"Antimicrob Agents Chemother. (Jul. 2009) 53(7):2799-2803.
Kint et al., "New-found fundamentals of bacterial persistence", Trends Microbiol. (2012) 20(12):577-585.
Kose et al., "Synthesis of photochromic 2,3-bis(5-methyl-2-phenyl-4-thiazolyl)-1,4-naphthoquinone derivatives", J Photochem Photobiol. A: Chemistry. (2011) 219(1):58-61.
Kotha et al., "Recent applications of the suzuki-miyaura cross-coupling reaction in organic synthesis", Tetrahedron (2002) 58:9633-9695.
Kumar et al., "Synthesis of intermediates for the lactone moiety of mevinic acids via tellurium chemistry", J. Org. Chem., (1994) 59(17):4760-4764.
Kumar et al., "Development of Practical Methodologies for the Synthesis of Functionalized Benzoboroxoles", Tetrahedron Lett. (Aug. 25, 2010) 51(34):4482-4485.
Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.
Kuti et al., "Use of Monte Carlo simulation to design an optimized pharmacodynamic dosing strategy for meropenem", J Clin Pharmacol. (Oct. 2003) 43(10:1116-1123.
Laitar et al., "Catalytic diboration of aldehydes via insertion into the copper-boron bond", J Am Chem Soc. (2006) 128(34):11036-11037.
Lapuebla et al., "Activity of Meropenem Combined with RPX7009, a Novel beta-Lactamase Inhibitor, against Gram-Negative Clinical Isolates in New York City", Antimicrob Agents Chemother. (Aug. 2015) 59(8):4856-4860.
Lee et al., "Vicinal Diboronates in High Enantiomeric Purity through Tandem Site-Selective NHC-Cu-Catalyzed Boron-Copper Additions to Terminal Alkynes", J Am Chem Soc. (Dec. 2009) 131(51):18234-18235.
Li et al, "Novel macrocyclic HCV NS3 protease inhibitors derived from α-amino cyclic boronates", Bioorganic Med Chem Lett. (2010) 20:5695-5700.
Li et al., "Synthesis and evaluation of novel alpha-amino cyclic boronates as inhibitors of HCV NS3 protease", Bioorg Med Chem Lett. (2010) 20:3550-3556.
Li et al., "Stereoselective total synthesis of etnangien and etnangien methyl ester", J Org Chem. (2010) 75(8):2429-2444.
Liang et al., "The Efficient Copper(I) (Hexabenzyl)tren Catalyst and Dendritic Analogues for Green "Click" Reactions between Azides and Alkynes in Organic Solvent and in Water: Positive Dendritic Effects and Monometallic Mechanism", Advance Syn Catal. (2011) 1353(18): 3434-3450.
Lima et al., "Bioisosterism: A Useful Strategy for Molecular Modification and Drug Design", Curr Med Chem. (2005) 12:23-49.

(56) References Cited

OTHER PUBLICATIONS

Liu et al., "Selective Protein tyrosine phosphatase 1B inhibitors: Targeting the second phosphotyrosine binding site with non-carboxylic acid-containing ligands", J Med Chem. (2003) 46(16):3437-3440.

Liu et al., "Application of Stereoselective Ether Transfer to the Synthesis of Isotactic Polyethers", J Org Chem. (2010) 75(12):3953-3957.

Livermore et al., "Activities of NXL104 combinations with Ceftazidime and Aztreonam against Carbapenemase-producing Enterobacteriaceae", Antimicr Agents Chemother. (2011) 55(1):390-394.

Lodise et al., "Penetration of meropenem into epithelial lining fluid of patients with ventilator-associated pneumonia", Antimicrob Agents Chemother. (Apr. 2011) 55(4):1606-1610.

Malfertheiner et al., "Current concepts in the management of Helicobacter pylori infection: the Maastricht III Consensus Report", Gut (2007) 56(6):772-781.

Matteson et al., "Iodomethaneboronic Esters and Aminomethaneboronic Esters", J Organomet. Chem. (1979) 170:259-264.

Matteson et al., "A Directed Chiral Synthesis of Amino Acids from Boronic Esters", Tetrahedron Lett. (1987) 28(39):4499-4502.

Matteson, D.S., "Asymmetric Synthesis with Boronic Esters", Acc Chem Res. (1988) 21(8):294-300.

Matteson, "Boronic esters in stereodirected synthesis", Tetrahedron (1989) 45(7):1859-1885.

Matteson et al., "A stereospecific convergent coupling of nucleophilic and electrophilic chiral carbons", J. Am. Chem. Soc. (1989) 111:4399-4402.

Matteson et al., "Synthesis of asymmetrically deuterated glycerol and dibenzylglyceraldehyde via boronic esters", J. Am. Chem. Soc. (1990) 112:3964-3969.

Matteson et al., "(Alkoxyalkyl)boronic Ester Intermediates for Asymmetric Synthesis", Organometallics (1996) 15:152-163.

Matteson, "Alpha-Halo Baronic Esters in Asymmetric Synthesis", Tetrahedron (1998) 54(36):10555-10607.

Matteson et al., "Glass-Catalyzed Conversion of Boronic Esters of Asymmetric Diols to Diol Sulfites and Amine Complexes of Boron Halides", Oranometallics (2001) 20(13):2920-2923 & supporting Information (9 pages).

Matteson et al., "Cesium Alkyltrifluoroborates from Asymmetric Boronic Esters" Synlett (Jul. 2006) 20:3501-3503.

Matteson et al., "Synthesis of a (Beta-acetamido-alpha-acetoxyethyl) boronic ester via azido boronic esters", J Organomet Chem. (2008) 693:2258-2262.

Meanwell, "Synopsis of some recent tactical application of bioisosteres in drug design" J. Med. Chem. (2011) 54:2529-2591.

Mendoza et al., "Bis(phenylthio)methaneboronic Esters as Sources of Carbanions and Ketene Thioacetals", J Org Chem. (1979) 44(8):1352-1354.

Micalizio et al., "A Boronic Ester Annulation Strategy for Diversity-Oriented Organic Synthesis", Angew Chem Int Ed Engl. (2002) 41(1):152-154.

Montalbetti et al., "Amide bond formation and peptide coupling", Tetrahedron (2005) 61:10827-10852.

Montefour et al., "Acinetobacter baumannii: an emerging multidrug-resistant pathogen in critical care", Crit Care Nurse (2008) 28(1):15-25.

Morandi et al., "Structure-based optimization of cephalothin-analogue boronic acids as beta-lactamase inhibitors", Bioorg Med Chem. (2008) 16(3):1195-205. Epub Nov. 7, 2007.

Nema et al., "Excipients and Their Role in Approved Injectable Products: Current Usage and Future Directions", PDA J Pharm Sci Technol. (2011) 65(3):287-332.

Ness et al., "Structure-based design guides the improved efficacy of deacylation transition state analogue inhibitors of TEM-1 beta-Lactamase", Biochemistry (2000) 39(18):5312-5321.

Nordmann et al., How to Detect NDM-1 Producers, J. Clin. Micro. (2011) 49:718-721.

Panek et al., "Diastereoselectivity in the borane methyl sulfide promoted hydroboration of .alpha.-alkoxy-.beta. gamma.-unsaturated esters. Documentation of an alkoxy-directed hydroboration reaction", J. Org. Chem. (1992) 57(20):5288-5290.

Patani et al., "Bioisostensm: A Rational Approach in Drug Design", Chem Rev. (1996) 96:3147-3176.

Paterson et al., "Extended-Spectrum beta-Lactamases: a Clinical Update", Clin Microbiol Rev. (2005) 18(4):657-686.

Perez et al., "Why are we afraid of Acinetobacter baumannii?", Expert Rev Anti Infect Ther. (2008) 6(3):269-71.

Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34): 11825-11827.

Powell et al., "Compendium of excipients for parenteral formulations", PDA J Pharm Sci Technol. (1998) 52(5):238-311.

Reissig et al.,"High diastereoselection in the alkylation of siloxy-substituted methyl cyclopropanecarboxylates: consequence of a pyramidal ester enolate anion?", J. Am. Chem. Soc. (1982) 104:1735-1737.

Robak et al., "Synthesis and applications of tert-butanesulfinamide", Chem Rev. (2010) 110(6):3600-3740.

Rodriguez-Martinez et al., "VIM-19, a Metallo-beta-lactamase with increased Carbapenemase Activity from *Escherichia coli* and Klebsiella pneumoniae", Antimicro Agents Chemother. (2010) 54(1):471-476.

Sabet et al., "In Vivo Efficacy of Carbavance (Meropenem/RPX7009) Against KPC-producing Enterobacteriaceae", Abstracts of the 54th Interscience Conference on Antimicrobial Agents and Chemotherapy (Sep. 5-9, 2014) F-958; 3 pages.

Sawyer et al., "Physical properties and synthetic utility of a-alkoxyorganolithium species as studied through ligand selectivity in tin-lithium exchange", J. Am. Chem. Soc. (1988) 110:842-853.

Selander et al., "Palladium-catalyzed allylic C-OH functionalization for efficient synthesis of functionalized allylsilanes", J Am Chem Soc. (2011) 133(3):409-411.

Shaffer, Robyn Kroop, "The Challenge of Antibiotic-Resistant *Staphylococcus*: Lessons from Hospital Nurseries in the mid-20th Century", Yale J Biol Med. (2013) 86:261-270.

Shao et al., "Asymmetric hydrogenation of 3,5-Dioxoesters catalyzed by Ru-binap complex: A short step asymmetric synthesis of 6-substituted 5,6-dehydro-2-pyrones", Tetrahedron (1993) 49(10):1997-2010.

Singh of al., "Asymmetric Homologation of Boronic Esters Bearing Azido and Silyloxy Substituents", J Org Chem. (2000) 65(20):6650-6653 and Erratum: J Org Chem. (2001) 66(22):7560.

Sliwka et al., "Synthetic Sulfur Carotenoids II: Optically Active Carotenoid Thiols", ; Tetrahedron: Asymmetry (1993) 4(3):361-368.

Solladiéet al., "First Stereocontrolled Synthesis of the (3S,5R,7R,10R,11R)-C1-C13 Fragment of Nystatin A(1)", J Org Chem. (1999) 64(15):5447-5452.

Souto et al., "Synthesis and biological characterization of the histone deacetylase inhibitor largazole and c7-modified analogues", J. Med. Chem. (2010) 53(12):4654-4667.

Spiegel et al., "CP-263,114 synthetic studies. Construction of an isotwistane ring system via rhodium carbenoid C-H insertion", Tetrahedron (2002) 58:6545-6554.

Sun et al., "Programmed Synthesis of a Contiguous Stereotriad Motif by Triple Stereospecific Reagent-controlled Homologation", Org Lttr. (Jul. 2013) 15(17):4500-4503.

Teo et al., "Efficient and highly aldehyde selective Wacker oxidation", Org Lett. (2012) 14(13):3237-3239.

Theuretzbacher et al., "Update on antibacterial and antifungal drugs—can we master the resistance crisis?", Curr Opin Pharmacol. (2011) 11:429-432.

Vasil'Ev et al., (1977): STN International HCAPLUS database, Columbus (OH), accession No. 1977: 72730; 1 page.

Vitor et al., "Rhenium(I)- and technetium(I) tricarbonyl complexes anchored by bifunctional pyrazole-diamine and pyrazole-dithioether chelators", J Organometal Chem (2004) 689(25):4764-4774.

(56) References Cited

OTHER PUBLICATIONS

Waley, Stephen G., "A quick method for the determination of inhibition constants", Biochem J. (1982) 205(3):631-633.
Walsh et al., "Metallo-beta-Lactamases: the Quiet before the Storm?", Clin Microbiol Rev. (2005) 18(2):306-325.
Wang et al., "Recognition and resistance in TEM beta-lactamase", Biochemistry (2003) 42(28):8434-8444.
Webb et al., "Metal catalysed hydroboration of vinyl sulfides, sulfoxides, sulfones, and sulfonates", J Mol Cat A: Chem. (2007) 275:91-100.
Wohlrab et al., "Total synthesis of plusbacin A3: a depsipeptide antibiotic active against vancomycin-resistant bacteria", J. Am. Chem. Soc. (2007) 129:4175-4177.
Xia et al., "Synthesis and SAR of novel benzoxaboroles as a new class of beta-lactamase inhibitors", Bioorg Med Chem Lett. (2011) 21:2533-2536.
Xie et al., "Group-assisted purification (GAP) chemistry for the synthesis of Velcade via asymmetric borylation of N-phosphinylimines", Beilstein J Org Chem (Mar. 2014) 10:746-751.
Yamamoto et al., "Iridium-catalyzed hydroboration of alkenes with pinacolborane", Tetrahedron (2004) 60:10695-10700.
Yanagisawa et al., "Nonpeptide angiotensin II receptor antagonists: synthesis, biological activities, and structure-activity relationships of imidazole-5-carboxylic acids bearing alkyl, alkenyl, and hydroxyalkyl substituents at the 4-position and their related compounds", J Med Chem. (1996) 39(1):323-338.
Yuen et al., "Deprotection of pinacolyl boronate esters via hydrolysis of intermediate potassium trifluoroborates", Tetrahed Lttr. (2005)46(46):7899-7903.
International Preliminary Report of Patentability dated Nov. 8, 2016 for International Application No. PCT/US2015/028613, filed Apr. 30, 2015.

SALTS AND POLYMORPHS OF CYCLIC BORONIC ACID ESTER DERIVATIVES AND THERAPEUTIC USES THEREOF

CROSS-REFERENCE TO RELATED APPLICATIONS

This application is the U.S. National Phase of International Application No. PCT/US2015/028265 entitled SALTS AND POLYMORPHS OF CYCLIC BORONIC ACID ESTER DERIVATIVES AND THERAPEUTIC USES THEREOF, filed Apr. 29, 2015 and published on Nov. 12, 2015 as WO 2015/171398, which claims the benefit of U.S. Provisional Application No. 61/988,524, filed May 5, 2014, the disclosure of which is incorporated herein by reference in its entirety

BACKGROUND OF THE INVENTION

Field of the Invention

The present invention relates to salts and polymorphs of cyclic boronic acid ester derivatives, compositions, their use and preparation as therapeutic agents for treating bacterial infection. In particular, the present invention relates to a potassium salt of 2-((3R,6S)-2-hydroxy-3-(2-(thiophen-2-yl)acetamido)-1,2-oxaborinan-6-yl)acetic acid.

Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of anti-bacterial therapy. The increase in antibiotic resistant strains has been particularly common in major hospitals and care centers. The consequences of the increase in resistant strains include higher morbidity and mortality, longer patient hospitalization, and an increase in treatment costs Various bacteria have evolved β-lactam deactivating enzymes, namely, β-lactamases, that counter the efficacy of the various β-lactams. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K.; et al. Crit. Care Nurse 2008, 28, 15; Perez, F. et al. Expert Rev. Anti Infect. Ther. 2008, 6, 269; Bou, G.; Martinez-Beltran, J. Antimicrob. Agents Chemother. 2000, 40, 428. 2006, 50, 2280; Bou, G. et al, J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other Enterobacteriaceae, *Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

Another mechanism of β-lactamase mediated resistance to carbapenems involves combination of permeability or efflux mechanisms combined with hyper production of beta-lactamases. One example is the loss of a porin combined in hyperproduction of ampC beta-lactamase results in resistance to imipenem in *Pseudomonas aeruginosa*. Efflux pump over expression combined with hyperproduction of the ampC β-lactamase can also result in resistance to a carbapenem such as meropenem.

Because there are three major molecular classes of serine-based β-lactamases, and each of these classes contains significant numbers of β-lactamase variants, inhibition of one or a small number of β-lactamases is unlikely to be of therapeutic value. Legacy β-lactamase inhibitors are largely ineffective against at least Class A carbapenemases, against the chromosomal and plasmid-mediated Class C cephalosporinases and against many of the Class D oxacillinases. Therefore, there is a need for improved β-lactamase inhibitors.

SUMMARY OF THE INVENTION

The present invention relates to antimicrobial agents and potentiators thereof. Some embodiments include salts, polymorphs, compounds, compositions, pharmaceutical compositions, use and preparation thereof. In particular, come embodiments relate to salts and polymorphs of cyclic boronic acid ester derivatives.

Some embodiments relate to a potassium salt of 2-((3R,6S)-2-hydroxy-3-(2-(thiophen-2-yl)acetamido)-1,2-oxaborinan-6-yl)acetic acid.

In some embodiments, the potassium salt is in a crystalline form exhibiting an X-ray powder diffraction pattern comprising at least three characteristic peaks selected from the group consisting of peaks at approximately 7.3°, 13.9° 16.9° 19.1° 20.8°, and 25.2°2θ.

Some embodiments include a pharmaceutical composition comprising the potassium salt described herein.

Some embodiments include a pharmaceutical composition prepared by dissolving the potassium salt described herein.

Some embodiments include a method of preventing a bacterial infection, comprising administering to a subject in need thereof, a composition described herein.

Some embodiments include a sterile container, comprising any one of the foregoing composition or any one of the foregoing potassium salt.

Some embodiments include a method of preparing a pharmaceutical composition for administration, comprising reconstituting the contents of any one of the foregoing the sterile container using a pharmaceutically acceptable liquid carrier.

Some embodiments relate to a process of making a crystalline form of a potassium salt of 2-((3R,6S)-2-hydroxy-3-(2-(thiophen-2-yl)acetamido)-1,2-oxaborinan-6-yl)acetic acid, comprising combining a purified 2-((3R,6S)-2-hydroxy-3-(2-(thiophen-2-yl)acetamido)-1,2-oxaborinan-6-yl)acetic acid with a solvent to form an intermediate solution; intermixing a potassium counterion with the intermediate solution; and isolating the crystalline form of the potassium salt of 2-((3R,6S)-2-hydroxy-3-(2-(thiophen-2-yl)acetamido)-1,2-oxaborinan-6-yl)acetic acid.

DETAILED DESCRIPTION OF THE PREFERRED EMBODIMENT

The present invention relates to salts and polymorphs of cyclic boronic acid ester derivatives and pharmaceutical compositions comprising the same. Some embodiments include uses thereof, including methods of preparation, and methods of treatment. In particular, the present invention relates to polymorphs of a salt of 2-((3R,6S)-2-hydroxy-3-(2-(thiophen-2-yl)acetamido)-1,2-oxaborinan-6-yl)acetic acid. More specifically, the present invention relates to polymorphs of a potassium salt of 2-((3R,6S)-2-hydroxy-3-(2-(thiophen-2-yl)acetamido)-1,2-oxaborinan-6-yl)acetic acid.

Compound 1

Compound 1 as used herein refers to 2-((3R,6S)-2-hydroxy-3-(2-(thiophen-2-yl)acetamido)-1,2 oxaborinan-6-yl) acetic acid as shown in the structure below.

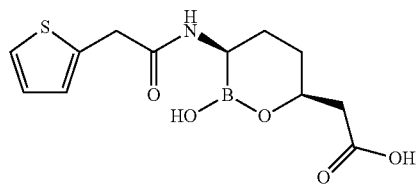

Compound 1

Compound 1 can be made by known methods such as the procedures described in US 2012/0040932, which is incorporated by reference in its entirety. More specifically, the skilled artisan given the disclosure in Example 1 of US 2012/0040932 is well equipped to prepare Compound 1.

Compound 1 contains a boronic acid moiety that is chemically stable in solutions having pH values between 2 and 8. The pKa of Compound 1 is measured to be 3.92. When combined with counterions such as potassium at suitable pH, Compound 1 can be converted into a salt.

Some embodiments relate to a pharmaceutically acceptable salt of 2-((3R,6S)-2-hydroxy-3-(2-(thiophen-2-yl)acetamido)-1,2-oxaborinan-6-yl)acetic acid. In some embodiments, the pharmaceutically acceptable salt is a potassium salt. In some embodiments, the pharmaceutically acceptable salt is a calcium salt. In some embodiments, the pharmaceutically acceptable salt is a magnesium salt.

Crystalline Form of Compound 1A

Figure 1:
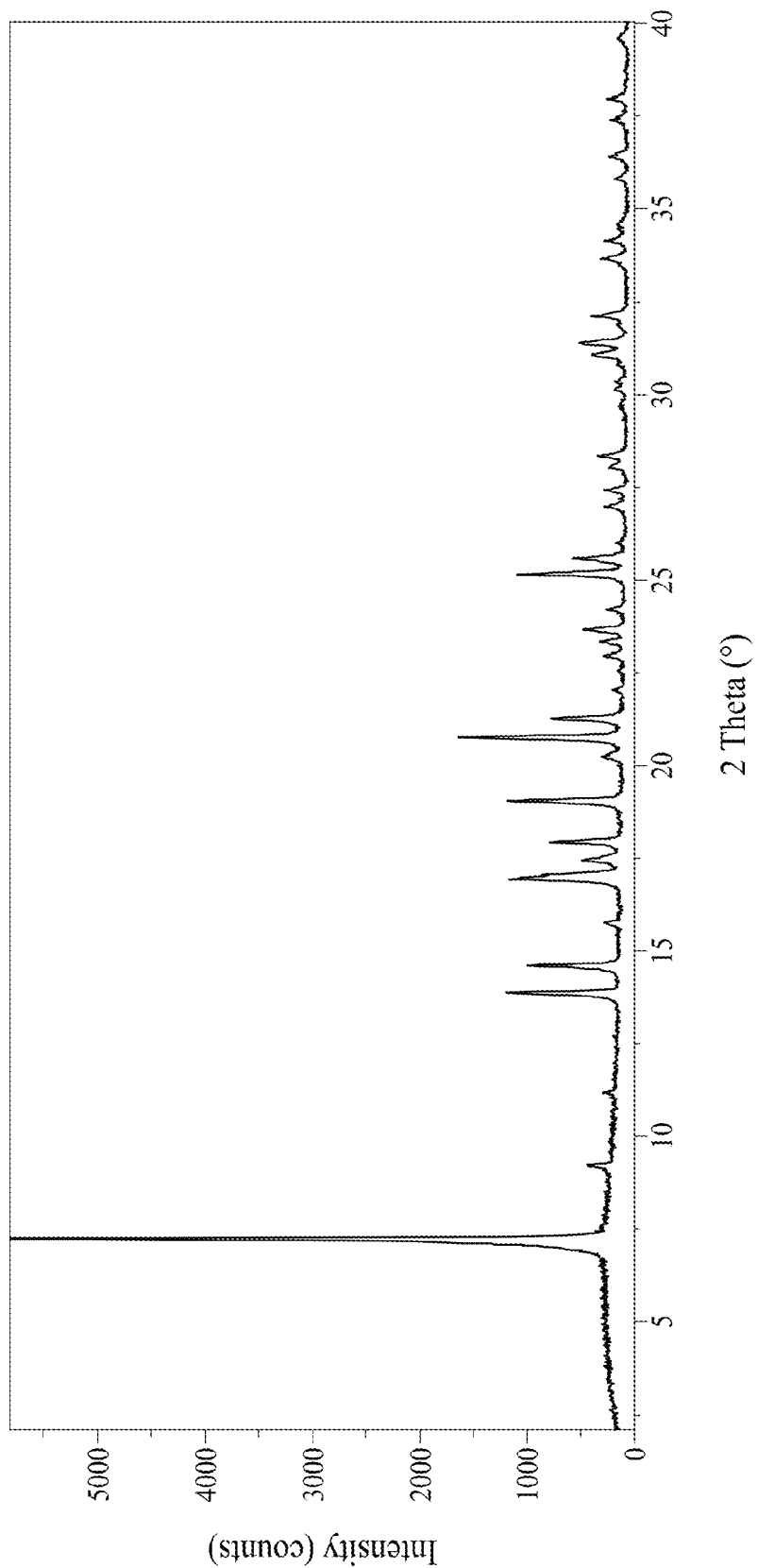
FIG. 1 is an X-ray powder diffraction (XRPD) pattern of the crystalline form of Compound 1A.

Compound 1A as used herein refers to the potassium salt of 2-((3R,6S)-2-hydroxy-3-(2-(thiophen-2-yl)acetamido)-1,2-oxaborinan-6-yl)acetic acid. Compound 1A can be made into a pure and stable crystalline form under controlled conditions. The X-ray powder diffraction (PXRD) pattern of Compound 1A is substantially the same as shown in FIG. 1, with corresponding tabulated peak data shown in Table 1.

TABLE 1

Peak Data of X-ray powder diffraction (PXRD) pattern of Compound 1A

| No. | Pos. [°2 Th.] | d-spacing [Å] | Height [cts] |
| --- | --- | --- | --- |
| 1 | 7.25 | 12.19 | 5999.35 |
| 2 | 9.23 | 9.59 | 213.77 |
| 3 | 13.87 | 6.38 | 1059.91 |
| 4 | 14.61 | 6.06 | 813.31 |
| 5 | 16.94 | 5.23 | 1005.45 |
| 6 | 17.07 | 5.19 | 664.12 |
| 7 | 17.45 | 5.08 | 358.32 |
| 8 | 17.94 | 4.94 | 635.36 |
| 9 | 19.05 | 4.66 | 1027.85 |
| 10 | 20.75 | 4.28 | 1510.77 |
| 11 | 21.26 | 4.18 | 654.04 |
| 12 | 23.34 | 3.81 | 216.52 |
| 13 | 23.66 | 3.76 | 379.78 |
| 14 | 25.15 | 3.54 | 964.68 |
| 15 | 25.58 | 3.48 | 484.34 |
| 16 | 28.33 | 3.15 | 246.72 |
| 17 | 31.05 | 2.88 | 304.67 |
| 18 | 31.38 | 2.85 | 435.25 |
| 19 | 32.10 | 2.79 | 311.25 |
| 20 | 33.65 | 2.66 | 239.27 |
| 21 | 34.12 | 2.63 | 196.90 |

Compound 1A is in a crystalline form exhibiting an X-ray powder diffraction pattern that includes at least three characteristic peaks selected from the group consisting of peaks at approximately 7.3°, 13.9°, 16.9, 19.1°, 20.8°; and 25.2°2θ. In some embodiments, the crystalline form of Compound 1A exhibits an X-ray powder diffraction pattern comprising at least peaks at 7.3°, 13.9°, 16.9°, 19.1°, 20.8°, and 25.2°2θ. In some embodiments, the crystalline form of Compound 1A exhibits an X-ray powder diffraction pattern comprising at least peaks at approximately 7.3°, 13.9°, 14.6°, 16.9°, 17.9°, 19.1°, 20.8°, 21.2°, 25.2°, and 25.6°2θ.

As is well understood in the art, because of the experimental variability when X-ray diffraction patterns are measured on different instruments, the peak positions are assumed to be equal if the two theta (2θ) values agree to within 0.2° (i.e., ±0.2°). For example, the United States Pharmacopeia states that if the angular setting of the 10 strongest diffraction peaks agree to within ±0.2° with that of a reference material, and the relative intensities of the peaks do not vary by more than 20%, the identity is confirmed. Accordingly, peak positions within 0.2° of the positions recited herein are assumed to be identical.

Figure 3:
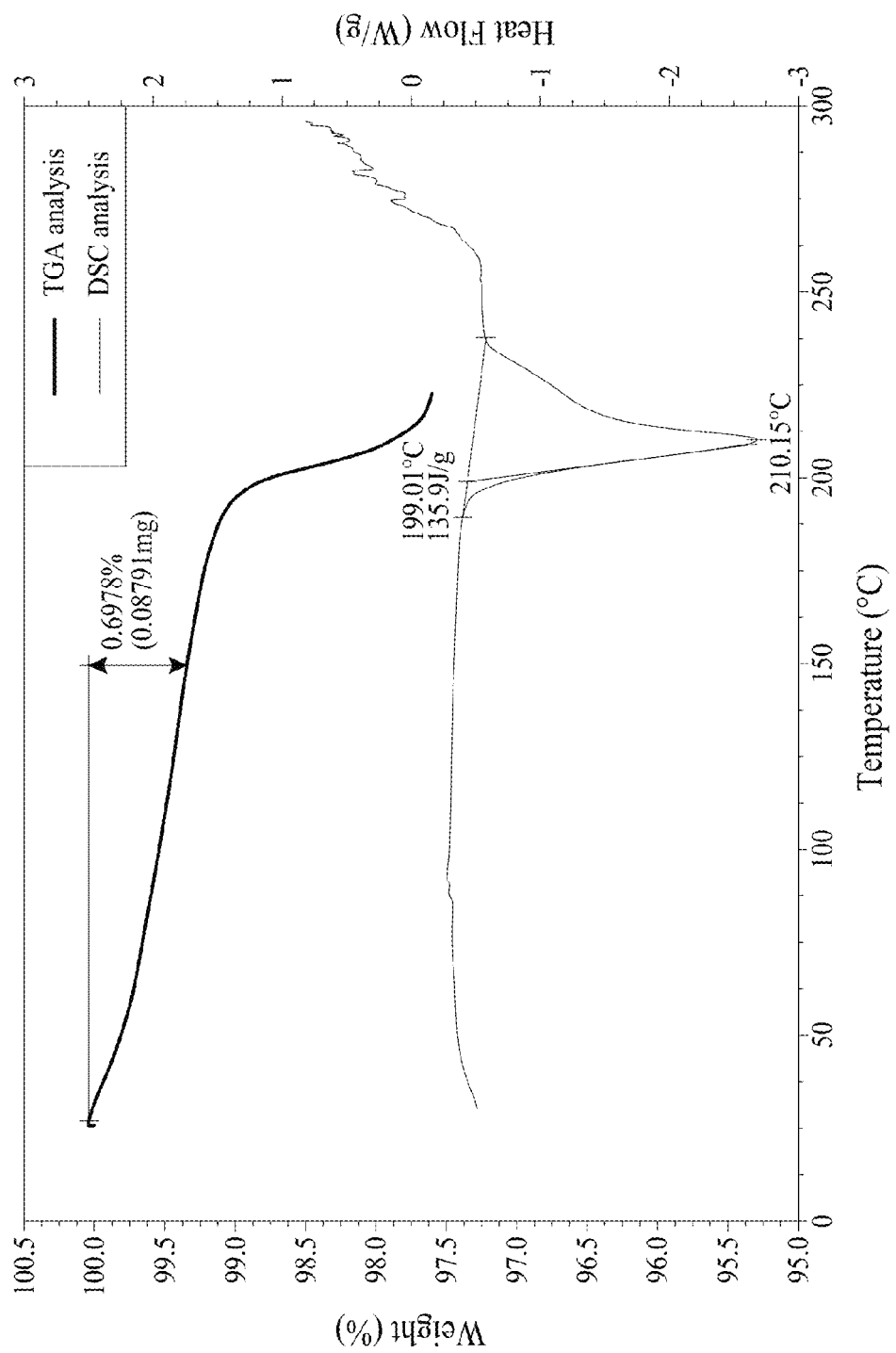
FIG. 3 shows thermo gravimetric (TGA) and digital scanning calorimetry (DSC) analysis results of the crystalline form of Compound 1A.

FIG. 3 shows digital scanning calorimetry (DSC) analysis results of the crystalline form of Compound 1A. As shown in FIG. 3, the crystalline form of the potassium salt has a melting point of 199.0° C.

Process of Making Crystalline Form of Compound 1A

One process for making a crystalline form of Compound 1A can include combining a purified Compound 1 with a solvent to form an intermediate solution; intermixing a potassium ion with the intermediate solution; and isolating the crystalline form of Compound 1A.

The source of potassium ion can vary. In some embodiment, the potassium ion is from potassium hydroxide. In some embodiment, the potassium ion is from potassium t-butoxide.

The solvent used for salt formation can vary depending on the source of the potassium ion and reaction conditions. In some embodiment, the solvent is selected from the group consisting of tetrahydrofuran, 1, 4-dioxane, acenitrile, acetone, ethyl acetate, methyl tert-butyl ether, water, and any combinations thereof. In some embodiment, the solvent is acetone or acenitrile. In some embodiment, the solvent is acetone. In some embodiment, the solvent is acenitrile.

Administration and Pharmaceutical Compositions

Some embodiments include pharmaceutical compositions comprising the potassium salt described herein and a pharmaceutically acceptable carrier. Such a composition can be administered to a subject as part of a therapeutic treatment.

Compound 1A described herein can be administered at a therapeutically effective dosage, e.g., a dosage sufficient to provide treatment for disease states described herein. Suitable dosage levels may be from about 0.1 mg/kg to about 200 mg/kg or more of body weight, from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

In some embodiments, the pharmaceutical composition described herein includes a unit dose from 0.01 mg to 10 g of the crystalline form of the potassium salt of 2-((3R,6S)-2-hydroxy-3-(2-(thiophen-2-yl)acetamido)-1,2-oxaborinan-6-yl)acetic acid. In some embodiments, the pharmaceutical composition described herein includes a unit dose from 0.1 mg to 5 g of the crystalline form of the potassium salt of 2-((3R,6S)-2-hydroxy-3-(2-(thiophen-2-yl)acetamido)-1,2-oxaborinan-6-yl)acetic acid. In some embodiments, the pharmaceutical composition described herein includes a unit dose from 0.1 mg to 2.5 g of the crystalline form of the potassium salt of 2-((3R,6S)-2-hydroxy-3-(2-(thiophen-2-yl)acetamido)-1,2-oxaborinan-6-yl)acetic acid. In some embodiments, the pharmaceutical composition described herein includes a unit dose from 1.5 g to 2.5 g of the crystalline form of the potassium salt of 2-((3R,6S)-2-hydroxy-3-(2-(thiophen-2-yl)acetamido)-1,2-oxaborinan-6-yl)acetic acid. In some embodiments, the pharmaceutical composition described herein includes a unit dose of less than 5 g, less than 4.5 g, less than 4 g, less than 3.5 g, less than 3 g, less than 2.5 g of the crystalline form of the potassium salt of 2-((3R,6S)-2-hydroxy-3-(2-(thiophen-2-yl)acetamido)-1,2-oxaborinan-6-yl)acetic acid. In some embodiments, the pharmaceutical composition described herein includes a unit dose more than 0.1 mg, more than 0.5 mg, more than 10 mg, more than 50 mg, more than 100 mg, more than 150 mg, more than 200 mg, more than 500 mg, more than 1 g, more than 2 g of the crystalline form of the potassium salt of 2-((3R,6S)-2-hydroxy-3-(2-(thiophen-2-yl)acetamido)-1,2-oxaborinan-6-yl)acetic acid.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarily, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety.

In addition to the selected compound useful as described above, come embodiments include compositions containing a pharmaceutically-acceptable carrier. The term "pharmaceutically-acceptable carrier", as used herein, means one or more compatible solid or liquid filler diluents or encapsulating substances, which are suitable for administration to a mammal. The term "compatible", as used herein, means that the components of the composition are capable of being commingled with the subject compound, and with each other, in a manner such that there is no interaction, which would substantially reduce the pharmaceutical efficacy of the composition under ordinary use situations. Pharmaceutically-acceptable carriers must, of course, be of sufficiently high purity and sufficiently low toxicity to render them suitable for administration preferably to an animal, preferably mammal being treated.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of

*theobroma*; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. These oral forms comprise a safe and effective amount, usually at least about 5%, with a maximum of about 90%, of the compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The resulting composition may be infused into the patient over a period of time. In various embodiments, the infusion time ranges from 5 minutes to continuous infusion, from 10 minutes to 8 hours, from 30 minutes to 4 hours, and from 1 hour to 3 hours. In one embodiment, the drug is infused over a 3 hour period. The infusion may be repeated at the desired dose interval, which may include, for example, 6 hours, 8 hours, 12 hours, or 24 hours.

The compositions for intravenous administration may be provided to caregivers in the form of one more solids that are reconstituted with a suitable diluent such as sterile water, saline or dextrose in water shortly prior to administration. Reconstituted concentrated solutions may be further diluted into a parenteral solutions having a volume of from about 25 to about 1000 ml, from about 30 ml to about 500 ml, or from about 50 ml to about 100 ml. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Kits for Intravenous Administration

Some embodiments include a sterile container having the composition described herein. Some embodiments include a sterile container having Compound 1A described herein. Some embodiments include a kit comprising a potassium salt described herein and an additional agent, such as an antimicrobial agent. In one embodiment, both components are provided in a single sterile container. In the case of solids for reconstitution, the agents may be pre-blended and added to the container simultaneously or may be dry-powder filled into the container in two separate steps. In some embodiments, an additional agent is a sterile crystalline product. In other embodiments, the additional agent is a lyophile. Non-limiting examples of agents to aid in lyophilization include sodium or potassium phosphates, citric acid, tartaric acid, gelatin, and carbohydrates such as dextrose, mannitol, and dextran. One embodiment includes non-sterile solids that are irradiated either before or after introduction into the container.

In the case of a liquid, the agents may be dissolved or dispersed in a diluent ready for administration. In another embodiment, the solution or dispersion may be further diluted prior to administration. Some embodiments include providing the liquid in an IV bag. The liquid may be frozen to improve stability.

In one embodiment, the container includes other ingredients such as a pH adjuster, a solubilizing agent, or a dispersing agent. Non-limiting examples of pH adjusters include NaOH, sodium carbonate, sodium acetate, HCl, and citric acid. In some embodiments, the liquid carrier is a saline solution.

The molar ratio of Compound 1A described herein to additional agent (e.g., antibacterial agent) may be from about 10:1 to 1:10, 8:1 to 1:8, 5:1 to 1:5, 3:1 to 1:3, 2:1 to 1:2, or about 1:1. In various embodiments the amount of compound described herein may be from 100 mg to 5 g, 500 mg to 2 g, or about 1 g. Similarly, in various embodiments the amount of additional agent may be from 100 mg to 5 g, 500 mg to 2 g, or about 1 g.

In an alternative embodiment, the two components may be provided in separate containers. Each container may include a solid, solution, or dispersion. In such embodiments, the two containers may be provided in a single package or may be provided separately. In one embodiment, the compound or composition described herein is provided as a solution while the additional agent (e.g., antibacterial agent) is provided as a solid ready for reconstitution. In one such embodiment, the solution of the compound or composition described herein is used as the diluent to reconstitute the other agent.

In case of preparing a pharmaceutical composition for administration, the contents of the sterile container can be reconstituted using a pharmaceutically acceptable liquid carrier. In some embodiments, the liquid carrier is a saline solution. In some embodiments, the liquid carrier is a dextrose solution. In some embodiments, the method of administration, comprising administering the reconstituted solution described herein intravenously to a subject.

Methods of Treatment

Some embodiments of the present invention include methods of treating bacterial infections with the compounds and compositions described herein. Some methods include administering a compound, composition, pharmaceutical composition described herein to a subject in need thereof. In some embodiments, a subject can be an animal, e.g., a mammal, a human. In some embodiments, the bacterial infection comprises a bacteria described herein. As will be appreciated from the foregoing, methods of treating a bacterial infection include methods for preventing bacterial infection in a subject at risk thereof.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. When combining the agents in a single dosage form, they may be physically mixed (e.g., by co-dissolution or dry mixing) or may form an adduct or be covalently linked such that they split into the two or more active ingredients upon administration to the patient. In another embodiment, the agents are administered sequentially. In one embodiment the agents are administered through the same route, such as orally. In another embodiment, the agents are administered through different routes, such as one being administered orally and another being administered i.v.

Examples of additional medicaments include an antibacterial agent, antifungal agent, an antiviral agent, an anti-inflammatory agent and an anti-allergic agent.

Some embodiments include co-administration of a compound, composition or pharmaceutical composition described herein with an antibacterial agent such as a β-lactam. Examples of such β-lactams include Amoxicillin, Ampicillin (e.g., Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (e.g., Dicloxacillin, Flucloxacillin), Oxacillin, Methicillin, Nafcillin, Faropenem, Biapenem, Doripenem, Ertapenem, Imipenem, Meropenem, Panipenem, Tomopenem, Razupenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, CXA-101, RWJ-54428, MC-04, 546, ME1036, BAL30072, SYN 2416, Ceftiofur, Cefquinome, Cefovecin, Aztreonam, Tigemonam, Carumonam, RWJ-442831, RWJ-333441, and RWJ-333442.

Preferred embodiments include β-lactams such as Ceftazidime, Biapenem, Doripenem, Ertapenem, Imipenem, Meropenem, ME1036, Tomopenem, Razupenem, and Panipenem.

Some embodiments include co-administration of the compounds, compositions and/or pharmaceutical compositions described herein with an additional agent, wherein the additional agent comprises a monobactam. Examples of monobactams include aztreonam, tigemonam, BAL 30072, SYN 2416 (BAL19764), and carumonam.

Some embodiments include co-administration of the compounds, compositions and/or pharmaceutical compositions described herein with an additional agent, wherein the additional agent comprises a Class A, B, C, or D beta-lactamase inhibitor. An example of a class B beta lactamase inhibitor includes ME1071 (Yoshikazu Ishii et al, "In Vitro Potentiation of Carbapenems with ME1071, a Novel Metallo-β-Lactamase Inhibitor, against Metallo-β-lactamase Producing *Pseudomonas aeruginosa* Clinical Isolates." Antimicrob. Agents Chemother. doi:10.1128/AAC.01397-09 (July 2010)). Other examples of beta-lactamase inhibitors administered as an additional agent include clavulanic acid, tazobactam, sulbactam, avibactam (NXL-104), MK-7655, and BAL29880. MK-7655 has the following structure:

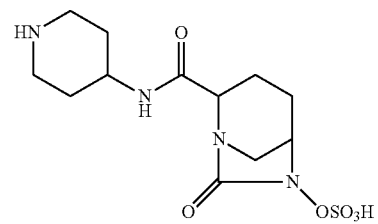

MK-7655

Indications

The compounds and compositions described herein can be used to treat bacterial infections. Bacterial infections that can be treated with the compounds, compositions and methods described herein can comprise a wide spectrum of bacteria. Example organisms include gram-positive bacteria, gram-negative bacteria, aerobic and anaerobic bacteria, such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms.

More examples of bacterial infections include *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*.

The following examples will further describe the present invention, and are used for the purposes of illustration only, and should not be considered as limiting.

EXAMPLES

Example 1. Salt Screening Study

Step 1. Purification and Characterization of Compound 1

Figure 6:
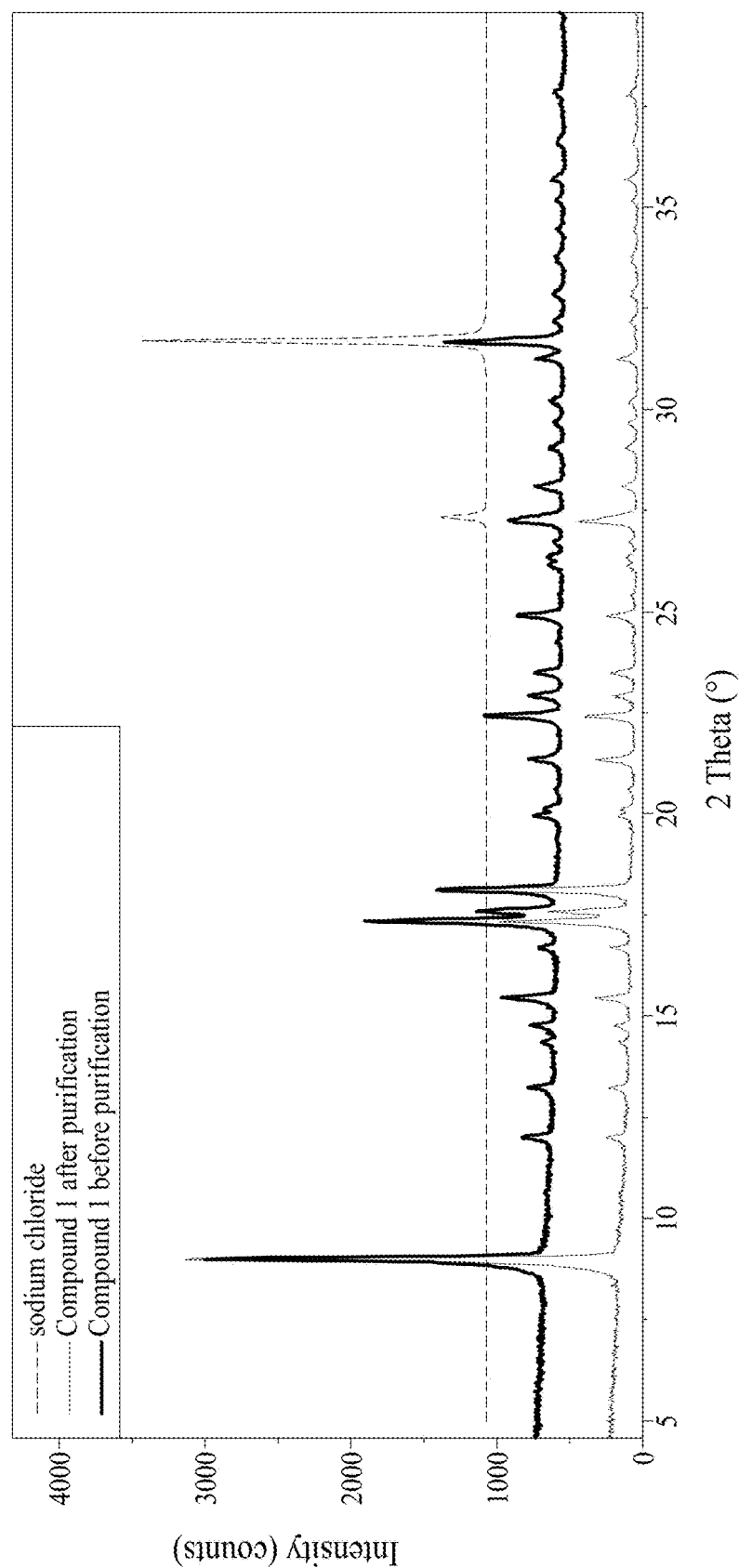
FIG. 6 shows the X-ray powder diffraction pattern of sodium chloride and Compound 1 before and after purification.

Compound 1, 2-((3R,6S)-2-hydroxy-3-(2-(thiophen-2-yl) acetamido)-1,2-oxaborinan-6-yl)acetic acid, was found to often contain undesired NaCl salt. FIG. 6 shows the PXRD pattern of the NaCl, Compound 1 before purification and after purification. As shown in FIG. 6, the peak at 31.6020 in the PXRD pattern is characteristic for the NaCl salt. The PXRD pattern for Compound 1 after purification shows significantly reduced or no presence of the NaCl salt.

During the purification process, compound 1 was combined with water (15.0 mL) and the suspension was stirred at room temperature for 4 hrs. The solids were isolated using a Büchner funnel and Whitman #1 filter paper. After filtration, the compound was air-dried for 15 hrs. The yield of the procedure was 87% by weight.

Figure 7:
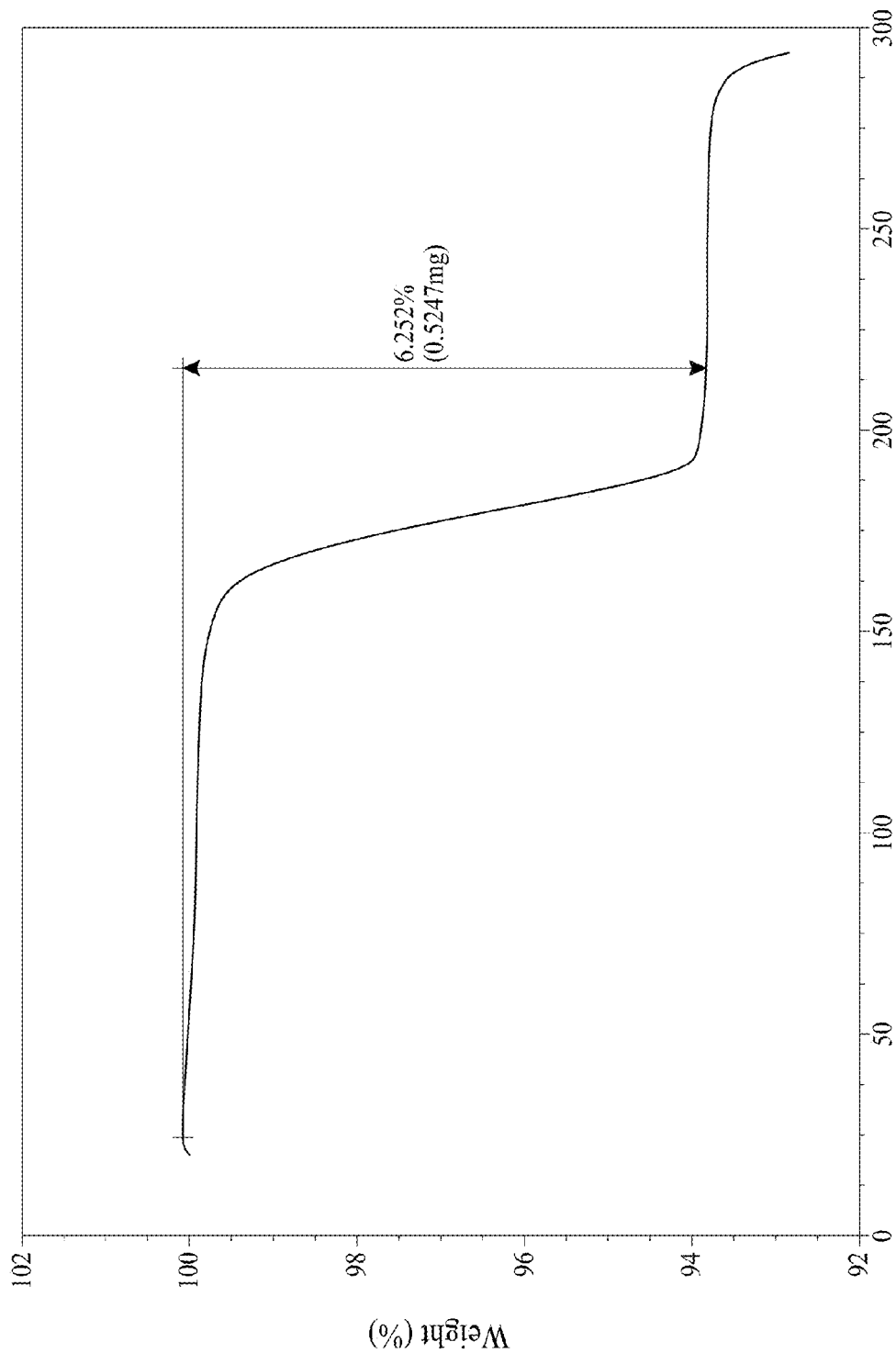
FIG. 7 is the TGA of Compound 1 after purification.
Figure 8:
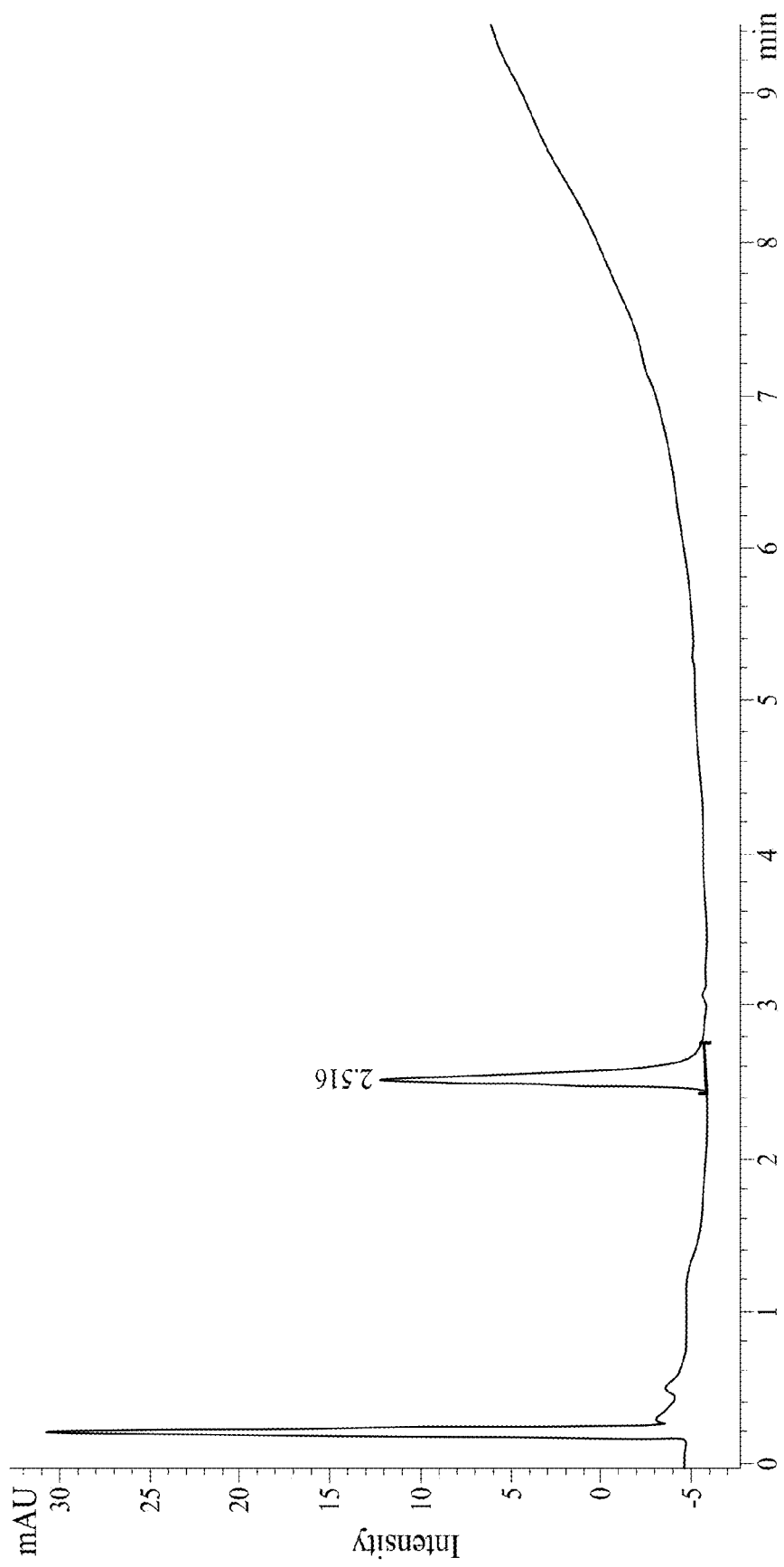
FIG. 8 shows a (HPLC) analysis of Compound 1 after purification.

After the purification step, the purified compound was analyzed using HPLC, PXRD and TGA. The PXRD pattern of the purified compound 1 is shown in FIG. 6. As shown in FIG. 6, the characteristic peaks of the NaCl salt in the purified compound disappeared as compared with the compound before purification. FIG. 7 shows the TGA trace of the purified compound 1. In FIG. 7, compound 1 underwent about 6.25% weight loss which was attributed to the loss of water due to a reversible reaction involving the boronic acid moiety. FIG. 8 is the HPLC analysis of the purified Compound 1. The HPLC chromatogram in FIG. 8 shows a retention peak of 2.52 for Compound 1 and no other peaks for NaCl or water. The analysis data confirmed that the material was 2-((3R,6S)-2-hydroxy-3-(2-(thiophen-2-yl)acetamido)-1,2-oxaborinan-6-yl)acetic acid and did not contain the undesired NaCl or crystallization solvent (water).

Step 2. Salt-Screening

During the salt-screening step, 60 combinations of seven counterions with nine solvent systems were tested. These combinations were subject to a series of crystallization modes and resulted in approximately 360 screening experiments.

Counterion Selection

Compound 1 has a pKa of 3.92 and was expected to form salts with strong bases. Because of a possible high projected dose (3 g/day) of compound 1, the counterion selection was limited to Class 1 molecules having low toxicity. (Handbook of Pharmaceutical Salts Properties, Selection, and Use P. H. Stahl, C. G. Wermuth, (2002) Wiley-VCH, Weinheim). Table 1 lists seven basic counterions selected for the salt screen study, their pKa values, and the corresponding stoichiometry and dosing strategies.

TABLE 1

Counterions used in the salt-screening study

| No. | Counterion | pKa3 | Equivalent | Dosing |
|---|---|---|---|---|
| 1 | Potassium hydroxide | ~14 | 1 | 3.6M in Water |
| 2 | Potassium t-butoxide | ~14 | 1 | 1.0M in t-BuOH |
| 3 | Choline hydroxide | >11 | 1 | 3.8M in Water |
| 4 | L-Lysine | 10.8; 9.2; 2.2 | 1 | 1.5M in Water |
| 5 | L-Arginine | 13.2; 9.1; 2.2 | 1 | 0.5M in Water |
| 6 | Meglumine | 8.0 | 1 | 1.5M in Water |
| 7 | Calcium hydroxide | 12.6; 11.6 | 0.5; 1 | Solid |
| 8 | Magnesium hydroxide | 11.4 | 0.5; 1 | Solid |

Solvent Selection

Nine solvent systems were evaluated in the Salt-screening study. The solvents were selected based on the solubility data accumulated during preceding studies. In addition, solvents represented a diverse set of polarities, dielectric constants, dipole moments, and hydrogen-bond donor/acceptor attributes to promote crystallization of salts. The solvents and rationale for their selection are summarized in Table 2.

TABLE 2

Solvents used in salt-screening study

| No. | Solvent | Attributes | Rationale for Selection |
|---|---|---|---|
| 1 | THEF Water (95:5% vol.) | Ether (Polar, Aprotic) Water (Polar, Protic) | High solubility of Compound 1 (S >> 1 mg/mL) |
| 2 | 1,4-Dioxane | Ether (Non-polar, Aprotic) | Moderate solubility of Compound 1 (S = 1-10 mg/mL) Afforded crystalline sodium salt |
| 3 | ACN | Nitrile (Polar, Aprotic) | Low solubility of Compound 1 (S < 1 mg/mL) |
| 4 | Acetone | Ketone (Polar, Aprotic) | Low solubility of Compound 1 (S < 1 mg/mL) Afforded crystalline sodium salt |
| 5 | Ethyl Acetate | Ester (Polar, Aprotic) | Low solubility of Compound 1 (S < 1 mg/mL) |
| 6 | MTBE | Ether (Non-polar, Aprotic) | Low solubility of Compound 1 (S < 1 mg/mL) Afforded crystalline sodium salt |
| 7 | Water | Water (Polar, Protic) | Low solubility of Compound 1 Expected high(er) solubility of a salt |
| 8 | ACN: Water (90:10% vol.) | Nitrile (Polar, Aprotic) Water (Polar, Protic) | Modest solubility of Compound 1 (S < 20 mg/mL) Use instead of MTBE in reactions with $Ca^{2+}$ and $Mg^{2+}$ counterions |
| 9 | Acetone: Water (50:50% vol.) | Ketone, (Polar, Aprotic) Water (Polar, Protic) | Low/modest solubility of Compound 1 Expected high(er) solubility of a salt |

Crystallization Modes

The salt-screening experiments were set up by combining 20.0±0.5 mg of Compound 1 with 300-500 µL of the solvent and the counterion in a stoichiometric amount. The screening studies were conducted in two stages.

In Stage 1, the samples involving counterion Nos. 1-6 listed in Table 1 were paired with solvent Nos. 1-6 listed in Table 2, whereas samples involving counterion Nos. 7 and 8 were paired with solvent Nos. 1-5 and 8.

All samples were subject to the following processing steps: 1) Stirring for 48 hrs while maintaining the cycling temperature between 5° C.-40° C.; 2) Stirring for 6 hrs at 40° C.; 3) Stirring for 24 hrs at 20° C.; 4) solvent addition (same solvent in the same amount); 5) Stirring for 72 hrs while maintaining the cycling temperature between 10° C.-30° C.; 6) Stirring for 72 hrs at 5° C.; 7) Solvent addition (the solvent type and amount was adjusted based on the observed solubility and the solvent can be the same solvent previously used, water, or DMSO); 8) Stirring for 24 hrs while maintaining the cycling temperature between 5° C.-30° C.; the solutions obtained from the above steps were 9) cooled to 5° C. and held at 5° C. for 72 hrs; 10) allowed to evaporate at ambient conditions over 3-14 days.

In Stage 2, a few samples that remained undissolved and amorphous in the first stage were 1) subjected to rapid solvent evaporation under vacuum; 2) dissolved in solvent Nos. 7-9 listed in Table 2; 3) cooled to 5° C. and held at 5° C. for 72 hrs; and 4) allowed to evaporate at ambient conditions over 3-7 days.

All samples were inspected visually and by Polarized light microscopy at every step listed above to check any formation of crystalline products. Any crystalline products obtained from these procedures were isolated by vacuum filtration and, where possible, analyzed by FT-Raman. Unique crystalline products were subjected to further analyses by PXRD, DSC, TGA-IR, and HPLC, as necessary.

Results of Salt-Screening Study

A majority of the experiments produced amorphous products, including oils, gums, and powders. Some crystalline screening products underwent partial or complete deliquescence upon isolation, some screening products were mixtures of unreacted components, and some screening products were mixtures of decomposed components. The counterion Nos. 3-8 listed in Table 1 did not yield a pure stable crystalline form of Compound 1A. Only the potassium salt of compound 1 yielded crystalline products. The results of some experiments are summarized in Table 3.

TABLE 3

Examples of Screening Crystalline Form

| Test | Counterions | Crystallization Method | Solvent | Results |
|---|---|---|---|---|
| 1 | Potassium hydroxide | Stage 1 | Acetone | G |
| 2 | Potassium hydroxide | Stage 1 | ACN | G |
| 3 | Potassium hydroxide | Stage 1 | MTBE | NG |
| 4 | Potassium hydroxide | Stage 1 | THF:Water (95:5 vol %) | NG |
| 5 | Potassium hydroxide | Stage 1 | 1,4-dioxane | G |
| 6 | Potassium hydroxide | Stage 1 | EtOAc | NG |
| 7 | Potassium hydroxide | Stage 2 | Water | NG |
| 8 | Potassium hydroxide | Stage 2 | ACN:Water (90:10 vol %) | NG |
| 9 | Potassium t-butoxide | Stage 1 | Acetone | G |
| 10 | Potassium t-butoxide | Stage 1 | ACN | NG |
| 11 | Potassium t-butoxide | Stage 1 | MTBE | NG |
| 12 | Potassium t-butoxide | Stage 1 | THF:Water (95:5 vol %) | NG |
| 13 | Potassium t-butoxide | Stage 1 | 1,4-dioxane | NG |
| 14 | Potassium t-butoxide | Stage 1 | EtOAc | NG |
| 15 | Choline hydroxide | Stage 1 | Acetone | NG |
| 16 | Choline hydroxide | Stage 1 | ACN | NG |
| 17 | Choline hydroxide | Stage 1 | MTBE | NG |
| 18 | Choline hydroxide | Stage 1 | THF:Water (95:5 vol %) | NG |
| 19 | Choline hydroxide | Stage 1 | 1,4-dioxane | NG |
| 20 | Choline hydroxide | Stage 1 | EtOAc | NG |
| 21 | Choline hydroxide | Stage 2 | Water | NG |
| 22 | Choline hydroxide | Stage 2 | ACN:Water (90:10 vol %) | NG |
| 23 | Choline hydroxide | Stage 2 | Acetone: Water (50:50 vol %) | NG |
| 24 | L-Lysine | Stage 1 | Acetone | NG |
| 25 | L-Lysine | Stage 1 | ACN | NG |
| 26 | L-Lysine | Stage 1 | MTBE | NG |
| 27 | L-Lysine | Stage 1 | THF:Water (95:5 vol %) | NG |
| 28 | L-Lysine | Stage 1 | 1,4-dioxane | NG |
| 29 | L-Lysine | Stage 1 | EtOAc | NG |
| 30 | L-Lysine | Stage 2 | Water | NG |
| 31 | L-Lysine | Stage 2 | ACN:Water (90:10 vol %) | NG |
| 32 | L-Lysine | Stage 2 | Acetone: Water (50:50 vol %) | NG |
| 33 | L-Arginine | Stage 1 | Acetone | NG |
| 34 | L-Arginine | Stage 1 | ACN | NG |
| 35 | L-Arginine | Stage 1 | MTBE | NG |
| 36 | L-Arginine | Stage 1 | THF:Water (95:5 vol %) | NG |
| 37 | L-Arginine | Stage 1 | 1,4-dioxane | NG |
| 38 | L-Arginine | Stage 1 | EtOAc | NG |
| 39 | L-Arginine | Stage 2 | Water | NG |
| 40 | L-Arginine | Stage 2 | ACN:Water (90:10 vol %) | NG |
| 41 | L-Arginine | Stage 2 | Acetone: Water (50:50 vol %) | NG |
| 42 | Meglumine | Stage 1 | Acetone | NG |
| 43 | Meglumine | Stage 1 | ACN | NG |
| 44 | Meglumine | Stage 1 | MTBE | NG |
| 45 | Meglumine | Stage 1 | THF:Water | NG |

TABLE 3-continued

Examples of Screening Crystalline Form

| Test | Counterions | Crystallization Method | Solvent | Results |
|---|---|---|---|---|
| 46 | Meglumine | Stage 1 | (95:5 vol %) 1,4-dioxane | NG |
| 47 | Meglumine | Stage 1 | EtOAc | NG |
| 48 | Meglumine | Stage 2 | Water | NG |
| 49 | Meglumine | Stage 2 | ACN: Water (90:10 vol %) | NG |
| 50 | Calcium hydroxide (0.5 equivalent) | Stage 1 | Acetone | NG |
| 51 | Calcium hydroxide (0.5 equivalent) | Stage 1 | ACN | NG |
| 52 | Calcium hydroxide (0.5 equivalent) | Stage 1 | THF:Water (95:5 vol %) | NG |
| 53 | Calcium hydroxide (0.5 equivalent) | Stage 1 | 1,4-dioxane | NG |
| 54 | Calcium hydroxide (0.5 equivalent) | Stage 1 | EtOAc | NG |
| 55 | Calcium hydroxide (0.5 equivalent) | Stage 2 | Water | NG |
| 56 | Calcium hydroxide (0.5 equivalent) | Stage 2 | ACN: (90:10 vol %) | NG |
| 57 | Calcium hydroxide (1 equivalent) | Stage 1 | Acetone | NG |
| 58 | Calcium hydroxide (1 equivalent) | Stage 1 | ACN | NG |
| 59 | Calcium hydroxide (1 equivalent) | Stage 1 | THF:Water (95:5 vol %) | NG |
| 60 | Calcium hydroxide (1 equivalent) | Stage 1 | 1,4-dioxane | NG |
| 61 | Calcium hydroxide (1 equivalent) | Stage 1 | EtOAc | NG |
| 62 | Calcium hydroxide (1 equivalent) | Stage 2 | Water | NG |
| 63 | Calcium hydroxide (1 equivalent) | Stage 2 | ACN:Water (90:10 vol %) | NG |
| 64 | Magnesium hydroxide (0.5 equivalent) | Stage 1 | Acetone | NG |
| 65 | Magnesium hydroxide (0.5 equivalent) | Stage 1 | ACN | NG |
| 66 | Magnesium hydroxide (0.5 equivalent) | Stage 1 | THF:Water (95:5 vol %) | NG |
| 67 | Magnesium hydroxide (0.5 equivalent) | Stage 1 | 1,4-dioxane | NG |
| 68 | Magnesium hydroxide (0.5 equivalent) | Stage 1 | EtOAc | NG |
| 69 | Magnesium hydroxide (0.5 equivalent) | Stage 2 | ACN:Water (90:10 vol %) | NG |
| 70 | Magnesium hydroxide (1 equivalent) | Stage 1 | Acetone | NG |
| 71 | Magnesium hydroxide (1 equivalent) | Stage 1 | ACN | NG |
| 72 | Magnesium hydroxide (1 equivalent) | Stage 1 | THF:Water (95:5 vol %) | NG |
| 73 | Magnesium hydroxide (1 equivalent) | Stage 1 | 1,4-dioxane | NG |
| 74 | Magnesium hydroxide (1 equivalent) | Stage 1 | EtOAc | NG |
| 75 | Magnesium hydroxide (1 equivalent) | Stage 2 | Water | NG |
| 76 | Magnesium hydroxide (1 equivalent) | Stage 2 | ACN:Water (90:10 vol %) | NG |
| 77 | Magnesium hydroxide (1 equivalent) | Stage 2 | Acetone: Water (50:50 vol %) | NG |
| 78 | Magnesium hydroxide (1 equivalent) | Stage 2 | Acetone: Water (50:50 vol %) | NG |
| 79 | Magnesium hydroxide (1 equivalent) | Stage 2 | Acetone: Water (50:50 vol %) | NG |
| 80 | Magnesium hydroxide (1 equivalent) | Stage 2 | Acetone: Water (50:50 vol %) | NG |
| 81 | Magnesium hydroxide (1 equivalent) | Stage 2 | Acetone: Water (50:50 vol %) | NG |
| 82 | Magnesium hydroxide (1 equivalent) | Stage 2 | Acetone: Water (50:50 vol %) | NG |
| 83 | Magnesium hydroxide (1 equivalent) | Stage 2 | Acetone: Water (50:50 vol %) | NG |

G—pure and stable crystalline form yielded
NG—no pure and stable crystalline form yielded Table 3 only listed 83 examples of the approximately 360 screening experiments performed using various combinations of counterions, solvent systems, and crystallization mode. Most of the screening experiments produced amorphous powders, oils, gums. For example, those experiments that involved calcium and magnesium counterions yielded products that were mixtures of the unreacted substrates. The FT-Raman and PXRD analysis of the products showed that no pure and stable crystalline salt was formed in the experiments involving calcium or magnesium counterions. For another example, when the screening experiments involved the solvent system of THF and Water (95:5 vol %) and a range of counterions (potassium, choline, calcium, and magnesium), the HPLC analysis confirmed significant decomposition present in those products.

Among the approximately 360 screening experiments performed, only the potassium salt Compound 1A in four experiments yielded a pure and stable crystalline form after long-term (>4 days) stirring of the initially amorphous products (gums and oils). The potassium salt was subsequently reproduced at 50 mg and 300 mg scales using seeding, which facilitated crystallization of the several hours of amorphous intermediate phase. The potassium salt may undergo deliquescence when isolated in open air; however, the deliquescence may be significantly reduced and/or eliminated by using the nitrogen blanket. Once a free-flowing powder was isolated, the powder was stable in open-air for at least 7 days.

In addition, only one crystalline form of the potassium salt was observed during the course of the presented study. This single crystalline form also showed that Compound 1A has a low propensity for polymorphism.

Example 2. Preparation of Potassium Salt at 50 mg Scale 48.7 mg of Compound 1 was combined with acetone (1.0 mL) in a 2-mL vial containing a stir bar. The suspension was stirred at 40° C. for 10 min and seeded with about 1 mg of potassium salt. 164.0 µL of potassium t-butoxide (1.0 eq. of compound 1; 1.0M solution in t-BuOH) was added in five aliquots: 10 µL, 20 µL, 20 µL, 20 µL, 93 µL in every 5 min. Gum was formed upon the counterion addition. The sample was stirred for 15 hrs while the cycling temperature was maintained between 40° C.-45° C., during which the gum changed into a free-flowing suspension. The suspension was equilibrated at 5° C. for 30 min and the solids were isolated on a Buchner funnel under nitrogen blanket and allowed to dry for 30 min. The yield of this preparation procedure was 70% wt.

Example 3. Preparation of Potassium Salt at 300 mg Scale

Compound 1 (302.6 mg) was combined with ACN (15.0 mL) in a 20-mL vial containing a stir bar. The suspension was stirred at 50° C. for 30 min and seeded with about 3 mg of potassium salt. 256.7 μL of potassium hydroxide (0.9 eq. of compound 1; 3.57M aqueous solution) was added in eight aliquots: 20 μL, 20 μL, 20 μL, 20 μL, 20 μL, 50 μL, 50 μL, 56.7 μL in every 15 min. Partial conversion to a gum upon the counterion addition was observed. The suspension was stirred at 50° C. for 60 min, cooled to 5° C. at 0.1° C./min rate (7.5 hrs), and subjected to stirring while the cycling temperature was maintained between 40° C.-45° C. for 10 hrs. The temperature cycle involved holding at 40° C. for 1 hr followed by cooling at 0.5° C./min, and then holding at 5° C. for 2 hrs followed by heating to 40° C. at a maximum rate. The suspension was equilibrated at 5° C. for 2 hrs. The solids were isolated on a Buchner funnel under nitrogen blanket, allowed to dry for 60 min at room temperature and then at 40° C. under vacuum for 3 hrs. The yield of this procedure was 65% wt.

Example 4. Characterization of Potassium Salt

Figure 2:
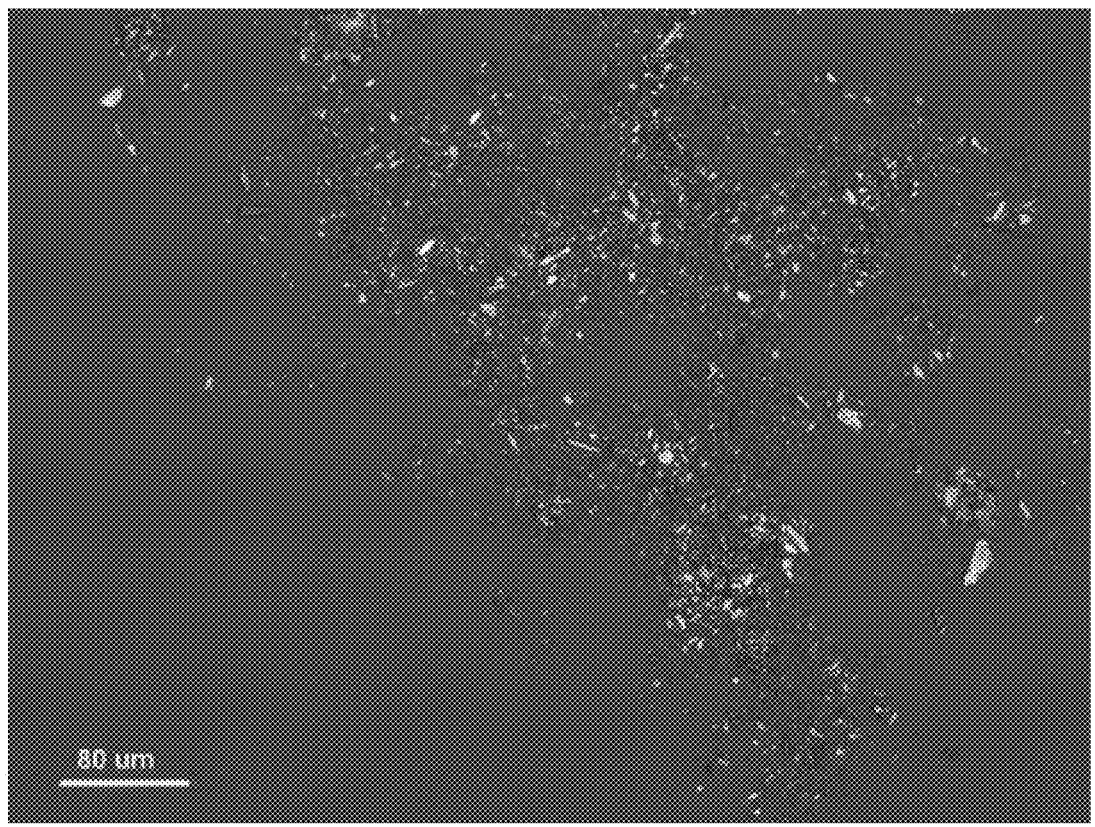
FIG. 2 shows a polarized light microscopy (PLM) image of a sample containing the crystalline form of Compound 1A.
Figure 4:
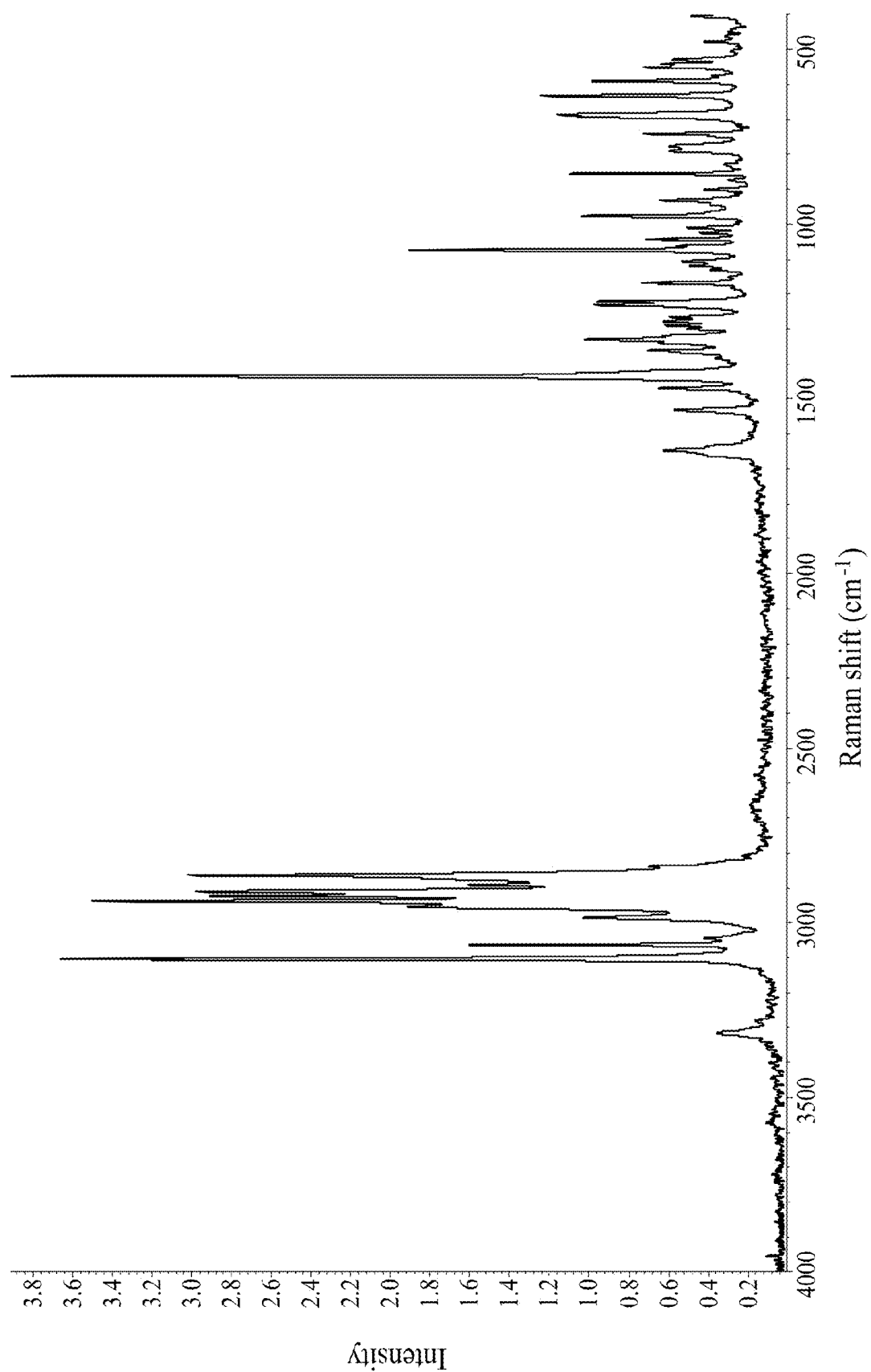
FIG. 4 shows a FT-Roman spectrum of the crystalline form of Compound 1A.
Figure 5:
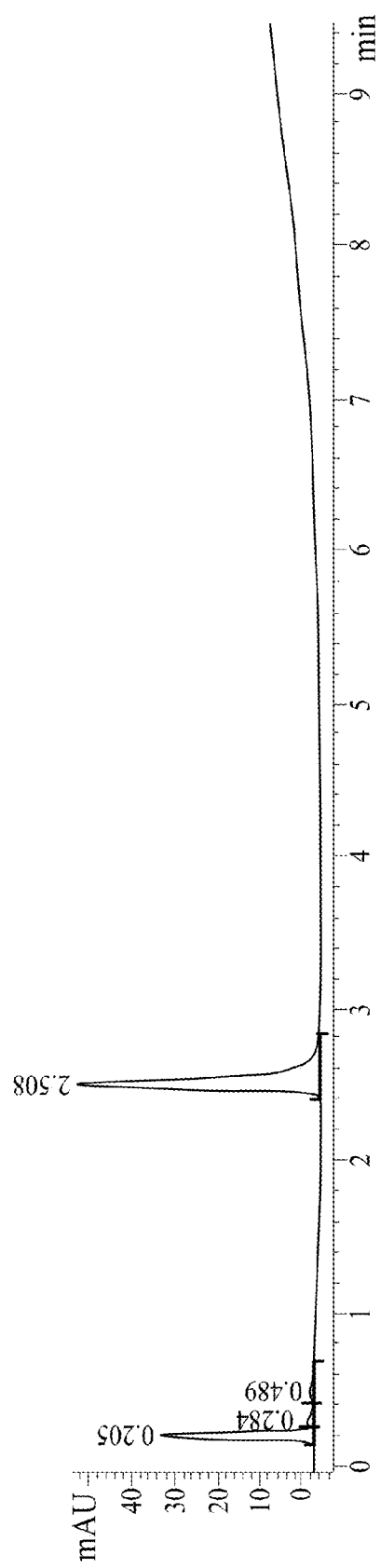
FIG. 5 shows a high-performance liquid chromatography (HPLC) analysis of the crystalline form of Compound 1A.

The potassium salt is a crystalline powder, as indicated by PXRD data in FIG. 1 and PLM image in FIG. 2. FIG. 3 is the TGA and DSC analysis and FIG. 4 shows the FT-Raman spectrum of the crystalline form of Compound 1A. The DSC trace in FIG. 3 shows a melting endotherm at 199.0° C. The TGA analysis of Compound 1A in FIG. 3 also indicates a gradual weight loss of ~0.7% wt. over the temperature range 25-150° C., which can be contributed to a loss of residual or surface solvent, and a major weight loss at temperatures above 160° C. that was attributed to decomposition. The HPLC analysis of the potassium salt as shown in FIG. 5 confirmed the absence of decomposition of Compound 1. The inductively coupled plasma atomic emission spectroscopy (ICP-AES) analysis confirmed the presence of potassium cations in the amount of 13.1% by weight. This result closely corresponds to a mono-salt composition because the theoretical content of 1 eq. of potassium is about 11.6% by weight.

Example 5. Studies of Sodium Salt

Studies of a possible sodium salt crystalline form were performed using purified compound 1 and amorphous sodium salt of compound 1 as the starting materials and explored diverse crystallization modes, solvents and temperatures.

The studies discovered five crystalline forms of the sodium salt (Groups A-E). Groups A and B were obtained from the screening experiments using compound 1 as the starting material. The PXRD pattern of Group A showed broad peaks indicative of poor crystallinity. The isolated material was found to be sticky and deliquesced readily (<5 minutes) when exposed to ambient conditions. PXRD pattern of Group B showed sharper peaks compared to Group A. The isolated Group B material was free flowing and easy to handle. Thermal analyses of Group B of sodium salt showed this form is a methanol/water solvate which converted to a hydrate on drying at 60° C.

Attempts to prepare Groups A and B using purified compound 1 led to two new crystalline forms of sodium salt (Groups D and E). These forms did not deliquesce when exposed to ambient conditions and were free-flowing solids. However, the DSC data of these two new forms showed broad endotherms below 150° C. indicative of a solvated/hydrated form.

Group C was isolated from a single crystallization experiment using amorphous sodium salt as the input. Group C of sodium salt showed physical properties similar to Group B and was found to be an acetone/water solvate which desolvated on drying at 60° C.

These results showed that the sodium salt of compound 1 is not a desirable crystalline form because of poor crystallinity, complicated polymorphism, poor thermal properties and hygroscopicity. In contrast, as described above, the potassium salt surprisingly demonstrated better crystallinity with a single crystalline form.

What is claimed is:

1. A potassium salt of 2-((3R,6S)-2-hydroxy-3-(2-(thiophen-2-yl)acetamido)-1,2-oxaborinan-6-yl)acetic acid.

2. The potassium salt of claim 1, wherein the potassium salt is in a crystalline form exhibiting an X-ray powder diffraction pattern comprising at least three characteristic peaks selected from the group consisting of peaks at approximately 7.3°, 13.9°, 16.9°, 19.1°, 20.8°, and 25.2°2θ.

3. The potassium salt of claim 2, exhibiting an X-ray powder diffraction pattern comprising at least peaks at approximately 7.3, 13.9°, 16.9°, 19.1°, 20.8°, and 25.2°2θ.

4. The potassium salt of claim 3, exhibiting an X-ray powder diffraction pattern comprising at least peaks at approximately 7.3°, 13.9°, 14.6°, 16.9°, 17.9°, 19.1°, 20.8°, 21.3°, 25.2°, and 25.6°2θ.

5. The potassium salt of claim 1, wherein said crystalline form has a melting point of 199.0° C.

6. The potassium salt of claim 1 having an X-ray powder diffraction pattern substantially the same as shown in FIG. 1.

7. A pharmaceutical composition comprising the potassium salt of claim 1 and a pharmaceutically acceptable excipient or a pharmaceutically acceptable liquid carrier.

8. The pharmaceutical composition of claim 7, further comprising an additional medicament selected from an antibacterial agent, antifungal agent, an antiviral agent, an antiinflammatory agent, or an anti-allergic agent.

9. The pharmaceutical composition of claim 8, wherein the additional medicament is a β-lactam antibacterial agent selected from Ceftazidime, Biapenem, Doripenem, Ertapenem, Imipenem, Meropenem, Panipenem, Aztreonam, Tigemonam, BAL30072, SYN 2416, or Carumonam.

10. The pharmaceutical composition of claim 7, comprising a unit dose from 0.1 mg to 5 g of the crystalline form of the potassium salt of 2-((3R,6S)-2-hydroxy-3-(2-(thiophen-2-yl)acetamido)-1,2-oxaborinan-6-yl)acetic acid.

11. A method of treating a bacterial infection, comprising administering to a subject in need thereof, a composition according to claim 7.

12. The method of claim 11, further comprising administering an additional medicament selected from an antibacterial agent, antifungal agent, an antiviral agent, an anti-inflammatory agent, or an anti-allergic agent.

13. The method of claim 12, wherein the additional medicament is a β-lactam antibacterial agent selected from Ceftazidime, Biapenem, Doripenem, Ertapenem, Imipenem, Meropenem, Panipenem, Aztreonam, Tigemonam, BAL30072, SYN 2416, or Carumonam.

14. The method of claim 11, wherein the subject is a mammal.

15. The method of claim 14, wherein the mammal is a human.

16. The method of claim 11, comprising administering the composition intravenously or orally to the subject.

17. A sterile container, comprising:
    the composition according to claim 7.

18. A sterile container, comprising:
    the potassium salt according to claim 1.

19. A method of preparing a pharmaceutical composition for administration, comprising reconstituting the contents of the sterile container of claim 17 using a pharmaceutically acceptable liquid carrier.

20. The method of any one of claim 19, wherein the liquid carrier is a saline solution or dextrose solution.

21. A process of making a crystalline form of a potassium salt of 2-((3R,6S)-2-hydroxy-3-(2-(thiophen-2-yl)acetamido)-1,2-oxaborinan-6-yl)acetic acid, comprising:
  combining a purified 2-((3R,6S)-2-hydroxy-3-(2-(thiophen-2-yl)acetamido)-1,2-oxaborinan-6-yl)acetic acid with a solvent to form an intermediate solution;
  intermixing a potassium ion with the intermediate solution; and
  isolating the crystalline form of the potassium salt of 2-((3R,6S)-2-hydroxy-3-(2-(thiophen-2-yl)acetamido)-1,2-oxaborinan-6-yl)acetic acid.

22. The process of claim 21, wherein the potassium ion is from potassium hydroxide or potassium t-butoxide.

23. The process of claim 21, wherein the solvent is selected from the group consisting of tetrahydrofuran, 1,4-dioxane, acenitrile, acetone, ethyl acetate, methyl tert-butyl ether, water, and any combinations thereof.

24. The process of claim 23, wherein the solvent is acetone or acenitrile.

* * * * *